United States Patent
Kitaoka et al.

(10) Patent No.: US 8,518,102 B2
(45) Date of Patent: Aug. 27, 2013

(54) STENT FOR PLACEMENT IN LIVING BODY, AND STENT DELIVERY SYSTEM

(75) Inventors: Takashi Kitaoka, Ashigarakami-gun (JP); Ryota Sugimoto, Ashigarakami-gun (JP)

(73) Assignee: Terumo Kabushiki Kaisha, Shibuya-Ku, Tokyo (JP)

( * ) Notice: Subject to any disclaimer, the term of this patent is extended or adjusted under 35 U.S.C. 154(b) by 78 days.

(21) Appl. No.: 13/074,554

(22) Filed: Mar. 29, 2011

(65) Prior Publication Data

US 2011/0196475 A1    Aug. 11, 2011

Related U.S. Application Data

(63) Continuation of application No. PCT/JP2009/066447, filed on Sep. 18, 2009.

(30) Foreign Application Priority Data

Sep. 29, 2008 (JP) .................................. 2008-251777

(51) Int. Cl.
*A61F 2/82* (2006.01)

(52) U.S. Cl.
USPC ........................................................ 623/1.15

(58) Field of Classification Search
USPC .................. 623/1.11–1.22; 606/191–200
See application file for complete search history.

(56) References Cited

U.S. PATENT DOCUMENTS

| | | | |
|---|---|---|---|
| 5,772,669 A * | 6/1998 | Vrba ............................. | 623/1.11 |
| 6,261,319 B1 * | 7/2001 | Kveen et al. ................. | 623/1.15 |
| 6,270,525 B1 | 8/2001 | Letendre et al. | |
| 7,235,097 B2 * | 6/2007 | Calisse et al. ................ | 623/1.15 |
| 7,645,297 B2 * | 1/2010 | Nissl ............................ | 623/1.15 |
| 8,230,913 B2 * | 7/2012 | Hart et al. .................... | 166/207 |
| 2001/0056298 A1 | 12/2001 | Brown et al. | |

(Continued)

FOREIGN PATENT DOCUMENTS

| JP | 4-075665 A | 3/1992 |
|---|---|---|
| JP | 11-505441 T | 5/1999 |

(Continued)

OTHER PUBLICATIONS

Extended European Search Report issued on Jul. 27, 2001 by the European Patent Office in corresponding European Patent Application No. 09 81 6136.

(Continued)

*Primary Examiner* — Suzette J Gherbi
(74) *Attorney, Agent, or Firm* — Buchanan Ingersoll & Rooney PC

(57) ABSTRACT

A stent includes a plurality of first wave-shaped struts extending in the axial direction of the stent and arranged in the circumferential direction of the stent, a plurality of second wave-shaped struts each located between the first wave-shaped struts, and one or more connecting struts each interconnecting the first wave-shaped strut and the second wave-shaped strut which are adjacent to each other, with the one or more connecting struts extending in the axial direction over a predetermined length. The apexes of the second wave-shaped struts are shifted a predetermined distance in the axial direction of the stent relative to the apexes of the first wave-shaped struts which are located close to the apexes in the circumferential direction of the stent and which are curved in the same direction as the apexes.

25 Claims, 16 Drawing Sheets

(56) References Cited

U.S. PATENT DOCUMENTS

| | | | |
|---|---|---|---|
| 2002/0042649 A1* | 4/2002 | Schaldach et al. | 623/1.15 |
| 2003/0004567 A1* | 1/2003 | Boyle et al. | 623/1.16 |
| 2003/0216807 A1 | 11/2003 | Jones et al. | |
| 2004/0138730 A1 | 7/2004 | Mitelberg et al. | |
| 2004/0193247 A1* | 9/2004 | Besselink | 623/1.15 |
| 2006/0116751 A1* | 6/2006 | Bayle et al. | 623/1.16 |
| 2006/0149356 A1* | 7/2006 | Kveen et al. | 623/1.16 |
| 2007/0067017 A1* | 3/2007 | Trapp | 623/1.16 |
| 2011/0196472 A1 | 8/2011 | Sugimoto et al. | |

FOREIGN PATENT DOCUMENTS

| | | |
|---|---|---|
| JP | 2001-137354 A | 5/2001 |
| JP | 2003-093519 A | 4/2003 |
| JP | 2004-167239 A | 6/2004 |
| JP | 2006-055330 A | 3/2006 |
| JP | 2006-346350 A | 12/2006 |
| WO | WO 03/063733 A1 | 8/2003 |
| WO | WO 2004/019822 A1 | 3/2004 |

OTHER PUBLICATIONS

B. Meier, "Plaque Sealing by Coronary Angioplasty," Heart, 2004 (month unknown), pp. 1395-1397, vol. 90.

International Search Report (PCT/ISA/210) issued on Oct. 20, 2009, by Japanese Patent Office as the International Searching Authority for International Application No. PCT/JP2009/066447.

Office Action issued by the European Patent Office on Jun. 25, 2012 in European Patent Application No. 09 816 136.7. (6 pages).

* cited by examiner

STENT FOR PLACEMENT IN LIVING BODY, AND STENT DELIVERY SYSTEM

This application is a continuation of International Application No. PCT/JP2009/066447 filed on Sep. 18, 2009, and claims priority to Japanese Application No. 2008-251777 filed on Sep. 29, 2008, the entire content of both of which is incorporated herein by reference.

TECHNOLOGICAL FIELD

The present invention relates to a stent for placement in living bodies and a stent delivery system for helping to improve a stenosed or occluded lesion generated in a living body lumen such as blood vessel, bile duct, trachea, esophagus, urethra, etc.

BACKGROUND PORTION

A stent for placement (indwelling) in living bodies is generally a tubular medical device which, for treatment of various diseases generated by stenosis or occlusion of a blood vessel or other living body lumen, is placed (put indwelling) in the stenosed or occluded lesion so as to dilate the lesion and secure the lumen at the lesion.

The following description of the stent is set forth describing one example of the use of the stent, namely in a blood vessel. This example should not be construed as a limitation.

The stent is a body which, for insertion from the outside into the inside of a living body, is relatively small in diameter at the time of insertion, and is expanded at the target stenosed or occluded lesion so as to be enlarged in diameter and to maintain the lumen at the lesion.

In general, stents are cylindrical bodies obtained by processing metallic wires or metallic pipes. A stent is mounted to a catheter or the like in a radially reduced state, is inserted into a living body, and is expanded at a target lesion by some method, to be fixed in close contact with the inner wall of the lumen at the lesion, thereby maintaining the lumen shape. Stents are classified by function and placement method as self-expandable stents and balloon-expandable stents. A balloon-expandable stent is a stent which itself does not have a self-expanding function or ability. The balloon-expandable stent is used together with a balloon in which the stent is mounted on the balloon and is inserted into a target lesion, and thereafter the balloon is dilated to expand (plastically deform) the stent by the expanding force of the balloon, whereby the stent is fixed in close contact with the inner surface of the target lumen. This type of stent requires the stent-expanding operation described above. On the other hand, a self-expandable stent is a stent which itself has a self-expanding function. The use of this self-expandable stent involves inserting the stent in a radially contracted state into a living body, and releasing the stent from the contracted state at a target part so as to allow the stent to return to its original expanded state, thereby being fixed in close contact with the inner wall of the lumen at the lesion and maintaining the lumen shape.

The purpose of the placement of a stent at present is to return a blood vessel stenosed for some reason to its original open (patent) state. In most cases, the stents are mainly for preventing or reducing the risk or extent of restenosis which might occur after such a procedure as PTCA. In recent years, for suppressing the probability of restenosis more securely, drug-eluting stents with such a drug as immunosuppressor or carcinostatic loaded thereon are used, and the effect thereof is generally known.

On the other hand, with regard to treatment of acute coronary syndromes represented by acute myocardial infarction and unstable angina or treatment of unstable plaque which is said to be pre-stage of the syndromes, an effective method has not yet been established. As to the treatment of acute coronary syndromes, the existing stents and drug-eluting stents are in contraindication in the status quo. The reason for this status lies in that the placement of a stent in a blood vessel including a large amount of thrombus cannot be free from the risk of stent malapposition and long-term thrombosis.

In relation to the unstable plaque, a thought called plaque sealing in which the plaque is stabilized by giving a stimulus to the relevant surface by balloon dilation or the like has been proposed by Meler et al (Heart 2004; 90: 1395-1398: Plaque sealing by coronary angioplasty). In recent years, it has been reported that plaque sealing is carried out by use of a self-expandable stent having a comparatively weak expanding force, in place of a balloon.

Most of the self-expandable stents are used in peripheral regions such as inferior-limb blood vessels and carotid arteries; in the coronary region, on the other hand, only the Radius stents made by Boston Scientific have been marketed in the past. The Radius stents have a form as shown in JP-T Hei 11-505441. In this type of stent, due to the properties of the stent, the positioning of the stent at the time of placement is difficult as compared with balloon-expandable stents. In fact, the occurrence of the so-called jumping phenomenon has been reported in which the stent is moved excessively from the sheath when placed (put indwelling).

The following has also been reported in academic meetings or the like. When conventional balloon-expandable stents and self-expandable stents having strong expanding forces are used in the plaque sealing, the stent placing operation itself has the risk of rupturing the plaque. Once the plaque is ruptured, there would be the fear of a risk of peripheral occlusion and/or an increase of inflammatory reactions at the relevant part. Therefore, such conventional stents are unsuited to plaque sealing.

Another stent has been proposed as described in Japanese Patent Laid-open No. 2003-93519. The stent disclosed in this document includes a plurality of wave-shaped struts extending in the axial direction of the stent from one end side to the other end side of the stent and arranged in the circumferential direction of the stent, and a plurality of connecting struts which each interconnect a pair of the wave-shaped struts adjacent to each other and which extend in the axial direction over a predetermined length, wherein each wave-shaped strut has an end portion joined to an end portion of the wave-shaped strut adjacent thereto. Since the stent is composed of the plurality of wave-shaped struts extending in the axial direction of the stent, the stent is flexible and may have possible application to plaque sealing.

In the stent described in Japanese Patent Laid-open No. 2003-93519, the apexes of the wave-shaped struts are located at the same positions with respect to the axial direction of the stent. In other words, the apexes of the plurality of wave-shaped struts are located in an annular fashion.

Studies conducted by the present inventors have led to the discovery that the stent described in Japanese Patent Laid-open No. 2003-93519 exhibits flexibility due to the use of the plurality of wave-shaped struts extending in the axial direction of the stent, but the stent as a whole lacks a smoothly bendable property. It is believed that this may be attributable to the fact that, in the above-described form of the stent, there is a large difference in physical properties between the annular regions where the apexes are present and the annular regions where the apexes are absent. It was found that, since the annular regions where the apexes are present are curved extremely flexibly as compared with the annular regions where the apexes are absent, the stent takes such a form that it is bent at its joint portions (the annular regions where the apexes are present).

SUMMARY

A stent for placement in living body comprises; a plurality of first wave-shaped struts and a plurality of second wave-shaped struts which together form a tubular member. The first wave-shaped struts extend in an axial direction of the tubular member from one end of the tubular member to an opposite end of the tubular member, and the plurality of first wave-shaped struts are arranged and spaced apart from each other in a circumferential direction of the tubular member. Each of the second wave-shaped struts are located between the first wave-shaped struts, extend in the axial direction of the tubular member from the one end of the tubular member to the opposite end of the tubular member, and are arranged and spaced apart in the circumferential direction of the tubular member. Each of the second wave-shaped struts are positioned between two circumferentially adjacent ones of the first wave-shaped struts. The stent also includes a plurality of connecting struts each interconnecting one of the first wave-shaped struts and one of the second wave-shaped struts which are circumferentially adjacent to each other; with the connecting struts extending in the axial direction over a predetermined length. The first and second wave-shaped struts each comprises a plurality of apexes, and the apexes of the second wave-shaped struts are shifted a predetermined distance in the axial direction of the tubular member relative to apexes of the first wave-shaped struts which are axially closest and curved in a common direction. The first wave-shaped struts each have an end portion at one end that is joined to an end portion at one end of the second wave-shaped struts.

The stent disclosed here is flexible and, as a whole, exhibits relatively smoothly bendable properties.

This stent has relatively high flexibility because it is composed of the plurality of wave-shaped struts extending in the axial direction of the stent. Because the apexes of the first wave-shaped struts and the apexes of the second wave-shaped struts do not overlap with each other in the axial direction of the stent, there are no annular regions in which both the apexes of the first and second wave-shaped struts are present in an annular pattern. Thus, the annular regions where the apexes are present are dispersed, and the number of the apexes present in each of the apex present regions is relatively small. As a result, a part largely different in physical properties from the other parts with reference to the axial direction of the stent is unlikely to be formed. Quite high flexibility and smoothly bendable properties are imparted to the whole stent in the axial direction.

The connecting struts are preferably configured so that each connecting strut: has one end connected in a vicinity of an inflection point of the first wave-shaped strut and an opposite end connected to the second wave-shaped strut in a region ranging from a position near one apex of the second wave-shaped strut and to a position slightly beyond the one apex of the second wave-shaped strut; extends in the axial direction; and is curved in the same direction as the one apex of the second wave-shaped strut.

The connecting struts can also be configured so that each connecting strut: has one end connected to the first wave-shaped strut at a point spaced from all of the apexes of the first wave-shaped strut and an opposite end connected to the second wave-shaped strut in a region ranging from a position near one apex of the second wave-shaped strut and to a position slightly beyond the one apex of the second wave-shaped strut; extends in the axial direction; and is curved in the same direction as the one apex of the second wave-shaped strut.

Each connecting strut can be curved in a different curving direction relative to the circumferentially closest connecting strut and can be curved in a common curving direction relative to the axially closest connecting strut.

The first wave-shaped struts preferably possess a wavelength and amplitude that are the same along the entire first wave-shaped strut except for the end portions of the first wave-shaped struts.

The second wave-shaped struts also possess a wavelength and amplitude that are the same along the entire second wave-shaped strut except for the end portions of the second wave-shaped struts.

The first and second wave-shaped struts can be configured such that the first wave-shaped struts and the second wave-shaped strut possess a common wavelength.

The first and second wave-shaped struts are preferably configured so that the phase of the second wave-shaped struts is shifted in the axial direction of the stent relative to the phase of the first wave-shaped struts.

The first wave-shaped strut can be configured so that at least a part of the first wave-shaped strut is different in waveform (amplitude and/or wavelength) from a remainder of the first wave-shaped strut. The second wave-shaped strut can also be configured so that at least a part of the second wave-shaped strut is different in waveform (amplitude and/or wavelength) from a remainder of the second wave-shaped strut.

The first and second wave-shaped struts can be configured to, possesses a common wavelength and a common amplitude, with the second wave-shaped struts shifted in phase in the axial direction of the stent relative to the first wave-shaped struts.

The first wave-shaped struts and the second wave-shaped struts can be arranged to extend parallel to a center axis of the stent.

The stent preferably includes a plurality of the connecting struts connecting each of the first wave-shaped struts to each of the circumferentially adjacent second wave-shaped struts. The connecting struts that connect a particular one of the first wave-shaped struts to a particular one of the circumferentially adjacent second wave-shaped struts are preferably arranged in spaced apart series in the axial direction of the stent. The connecting struts connecting each first wave-shaped strut to each circumferentially adjacent second wave-shaped strut can also be arranged in the circumferential direction of the tubular member.

The apexes of the first wave-shaped struts are preferably positioned in troughs of the circumferentially adjacent second wave-shaped struts, and the apexes of the second wave-shaped struts are preferably positioned in troughs of the circumferentially adjacent first wave-shaped struts.

The connecting struts are preferably curved in a circular arc shape possessing a radius of curvature equal to a radius of curvature of a curved part of the first wave-shaped strut or the second wave-shaped strut to which the connecting strut is connected.

The stent can be constructed such that the one end portion of each second wave-shaped strut is connected by a first joint section to the one end portion of the first wave-shaped strut on the one circumferential side of such second wave-shaped strut, and an opposite end portion of such second wave-shaped strut is connected by a second joint section to an opposite end portion of the first wave-shaped strut on the opposite circumferential side of such second wave-shaped strut. In addition, the first and second joint sections can each include a radiopaque marker.

Each of the first wave-shaped struts includes opposite end portions each connected to a different one of the second wave-shaped struts. The stent can also be provided with a surface configuration that accelerates endothelial growth.

The stent can be a self-expandable stent possessing a cylindrical shape. Such a stent can be delivered to the desired location by a stent delivery system comprising an inner tube and a sheath possessing a distal portion surrounding the inner tube so that the inner tube is positioned inside and covered by the distal portion of the sheath. The self expandable stent is mounted on the inner tube and positioned inside the distal portion of the sheath, with the sheath being movable in a proximal direction relative to the inner tube to discharge the stent.

Alternatively, the stent can be a balloon-expandable stent comprising a tubular body possessing a diameter sized for insertion into a lumen in a living body, and is outwardly expandable when a radially outwardly spreading force is exerted on the stent from inside the stent. This balloon-expandable stent can be used with a stent delivery system comprising a tubular shaft body section possessing a distal portion, and a foldable and dilatable balloon at a distal portion of the shaft body section. The balloon-expandable stent is mounted in surrounding relation to the balloon, is in a folded state and is outwardly expandable by dilation of the balloon.

According to another aspect, a stent for placement in living body comprises a plurality of sinusoidal first wave-shaped struts which are all commonly configured and a plurality of sinusoidal second wave-shaped struts which are all commonly configured, with the first wave-shaped struts and the second wave-shaped struts together forming a tubular member, and with the first wave-shaped struts circumferentially alternating with the second wave-shaped struts so that one of the second wave-shaped struts is positioned between each circumferentially adjacent pair of first wave-shaped struts and so that one of the first wave-shaped struts is positioned between each circumferentially adjacent pair of second wave-shaped struts. Each of the first wave-shaped struts extends in an axial direction of the tubular member from one end of the tubular member to an opposite end of the tubular member, and each of the first wave-shaped struts has a first end positioned at the one end of the tubular member and a second end positioned at the opposite end of the tubular member. Each of the first wave-shaped struts comprises a plurality of axially spaced apart first curved portions which are convexly curved towards one circumferential side of the first wave-shaped strut and a plurality of axially spaced apart second curved portions which are convexly curved towards an opposite circumferential side of the first wave-shaped struts. Each of the second wave-shaped struts extends in the axial direction of the tubular member from the one end of the tubular member to the opposite end of the tubular member, and each of the second wave-shaped struts has a first end positioned at the one end of the tubular member and a second end positioned at the opposite end of the tubular member. Each of the second wave-shaped struts comprises a plurality of axially spaced apart first curved portions which are convexly curved towards one circumferential side of the second wave-shaped strut and a plurality of axially spaced apart second curved portions which are convexly curved towards an opposite circumferential side of the second wave-shaped strut. The first and second curved portions of the first wave-shaped strut each possess an apex, the first and second curved portions of the second wave-shaped strut each possessing an apex, and each of the first wave-shaped struts is connected to each of the circumferentially adjacent second wave-shaped struts by at least one connecting strut. The first end of each respective first wave-shaped strut is connected to the first end of the second wave-shaped strut which is on the one circumferential side of the respective first wave-shaped strut, and the second end of each respective first wave-shaped strut is connected to the second end of the second wave-shaped strut which is on the opposite circumferential side of the respective first wave-shaped strut. Also, the apex of each first curved portion of the first wave-shaped struts is axially offset relative to an axially closest apex of the first curved portion of the circumferentially adjacent second wave-shaped strut.

DETAILED DESCRIPTION

Figure 1:
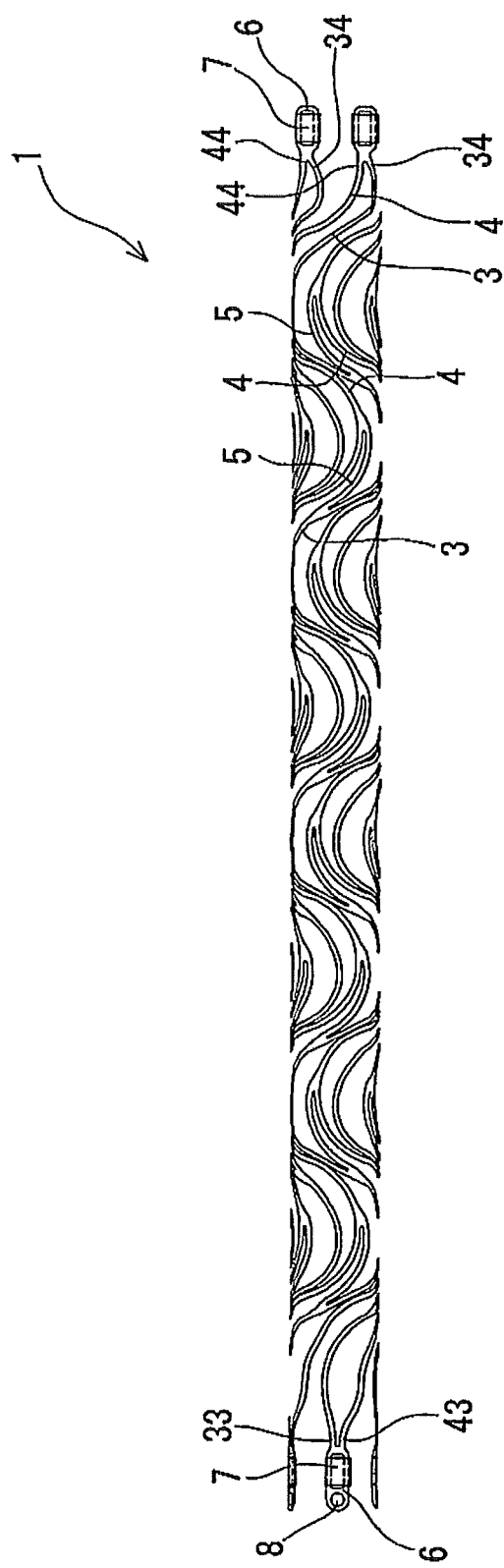
FIG. 1 is a front view of a stent for placement in living body according to one embodiment disclosed here.

FIGS. 1-8 illustrate a stent according to one embodiment disclosed here. The stent 1 is a stent for placement in living bodies and is configured to be tubular in shape (inclusive of substantially tubular). Generally speaking, the stent 1 includes: a plurality of first wave-shaped struts 3 each extending in the axial direction of the stent 1 from one end to the other end (an opposite end) of the stent 1 and arranged in the circumferential direction of the stent; a plurality of second wave-shaped struts 4 located between the first wave-shaped struts 3, each extending in the axial direction of the stent from one end to the other end (an opposite end) of the stent, and arranged in the circumferential direction of the stent; one or more connecting struts 5 each interconnecting the first wave-shaped strut 3 and the circumferentially adjacent second wave-shaped strut 4, with the one or more connecting struts 5 extending in the axial direction over a predetermined length. The first and second wave-shaped struts 3, 4 together form a tubular member.

In this example of the disclosed stent, the first wave-shaped struts 3 are sinusoidal (i.e., comprised of a series of waves or curved portions) and are commonly configured (i.e., all of the first wave-shaped struts possesses the same shape or configuration), the second wave-shaped struts 4 are sinusoidal and are commonly configured (i.e., all of the second wave-shaped struts possesses the same shape or configuration), and the first wave-shaped struts circumferentially alternate with the second wave-shaped struts so that one (and only one) of the second wave-shaped struts is positioned between each circumferentially adjacent pair of first wave-shaped struts and so that one (and only one) of the first wave-shaped struts is positioned between each circumferentially adjacent pair of second wave-shaped struts. Also, in this example of the disclosed stent, each of the first wave-shaped struts 3 includes axially spaced apart curved portions which are convexly curved towards one circumferential side of the first wave-shaped strut 3 and axially spaced apart curved portions which are convexly curved towards an opposite circumferential side of the first wave-shaped strut 3. Similarly, each of the second wave-shaped struts 4 includes axially spaced apart curved portions which are convexly curved towards one circumferential side of the second wave-shaped strut 3 and axially spaced apart curved portions which are convexly curved towards the other circumferential side (an opposite circumferential side) of the second wave-shaped strut 3.

The apexes 41, 42 of the curved portions of the second wave-shaped struts 4 are shifted a predetermined distance in the axial direction of the stent (tubular member) relative to those apexes 31, 32 of the curved portions of the first wave-shaped struts 3 which are located close to the apexes 41, 42 in the circumferential direction of the stent 1 and which are curved in the same direction as the apexes 41, 42. In addition, one end portion 34 of each of the first wave-shaped struts 3 is joined or connected to one end portion 44 of the circumferentially adjacent second wave-shaped strut 4, and the other end portion (an opposite end portion) 33 of each of the first wave-shaped struts 3 is joined or connected to the other end portion (an opposite end portion) 43 of the circumferentially adjacent second wave-shaped strut 4.

The stent in this embodiment is a so-called self-expandable stent possessing a cylindrical shape (inclusive of substantially cylindrical shape), compressed toward its center axis at the time of insertion into a living body, and expandable outwardly when placed (put indwelling) in the living body so that the stent is restored to its pre-compression shape. The stent may be a stent formed as a tubular body, possessing a diameter permitting insertion into a lumen in a living body, and expandable when a radially outwardly spreading force is exerted on the stent from the inside of the tubular body.

Figure 3:
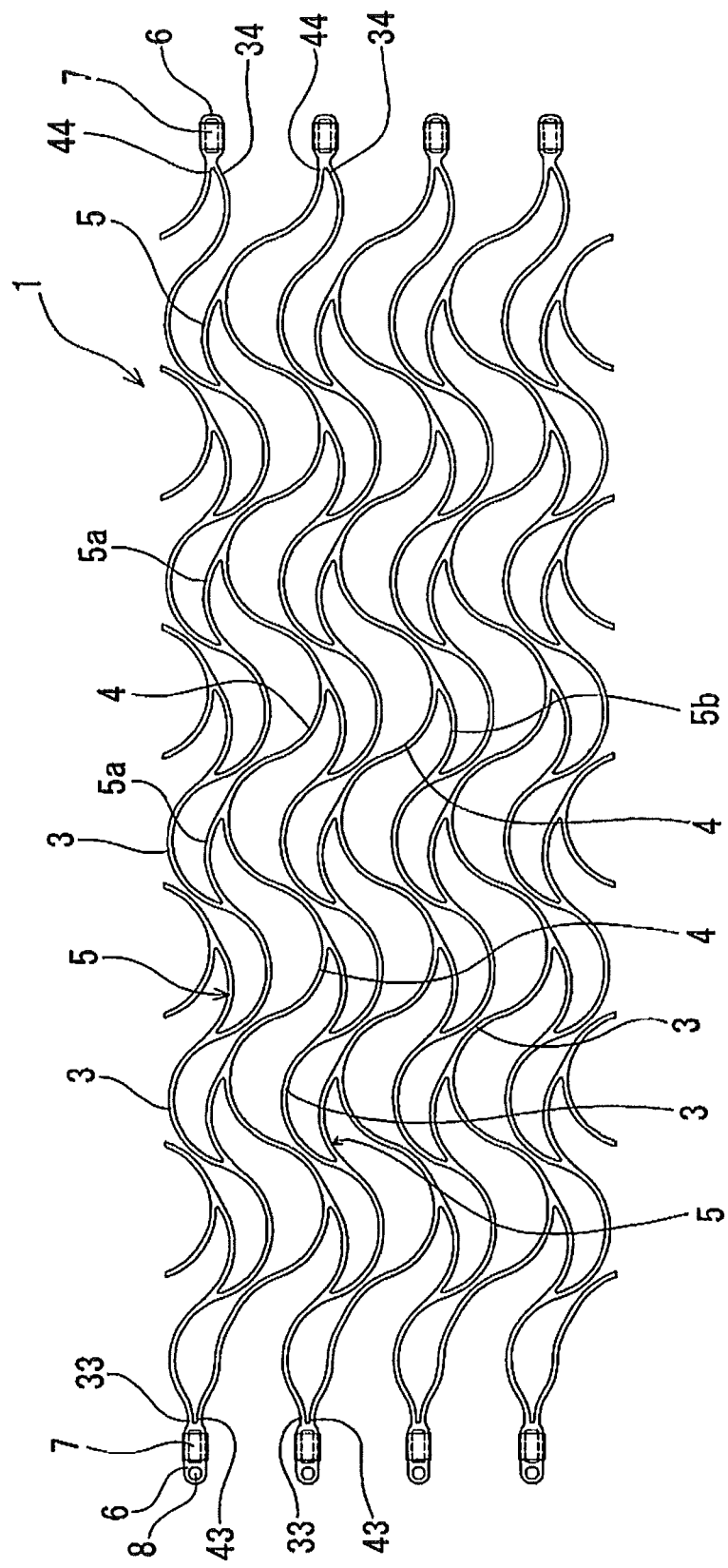
FIG. 3 is a development view, at the time of manufacturing, of the stent of FIG. 1.
Figure 5:
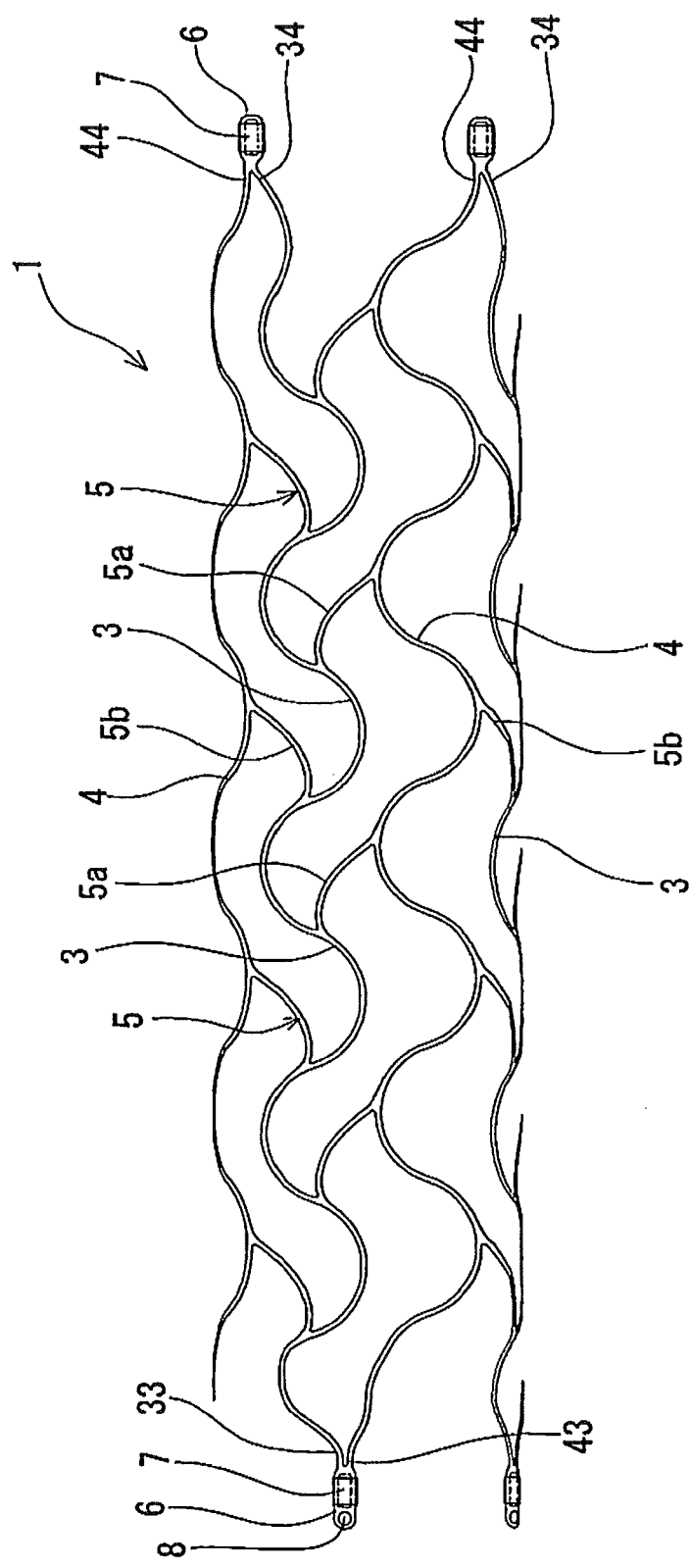
FIG. 5 is a front view of the stent of FIG. 1, in a maximally expanded state.
Figure 6:
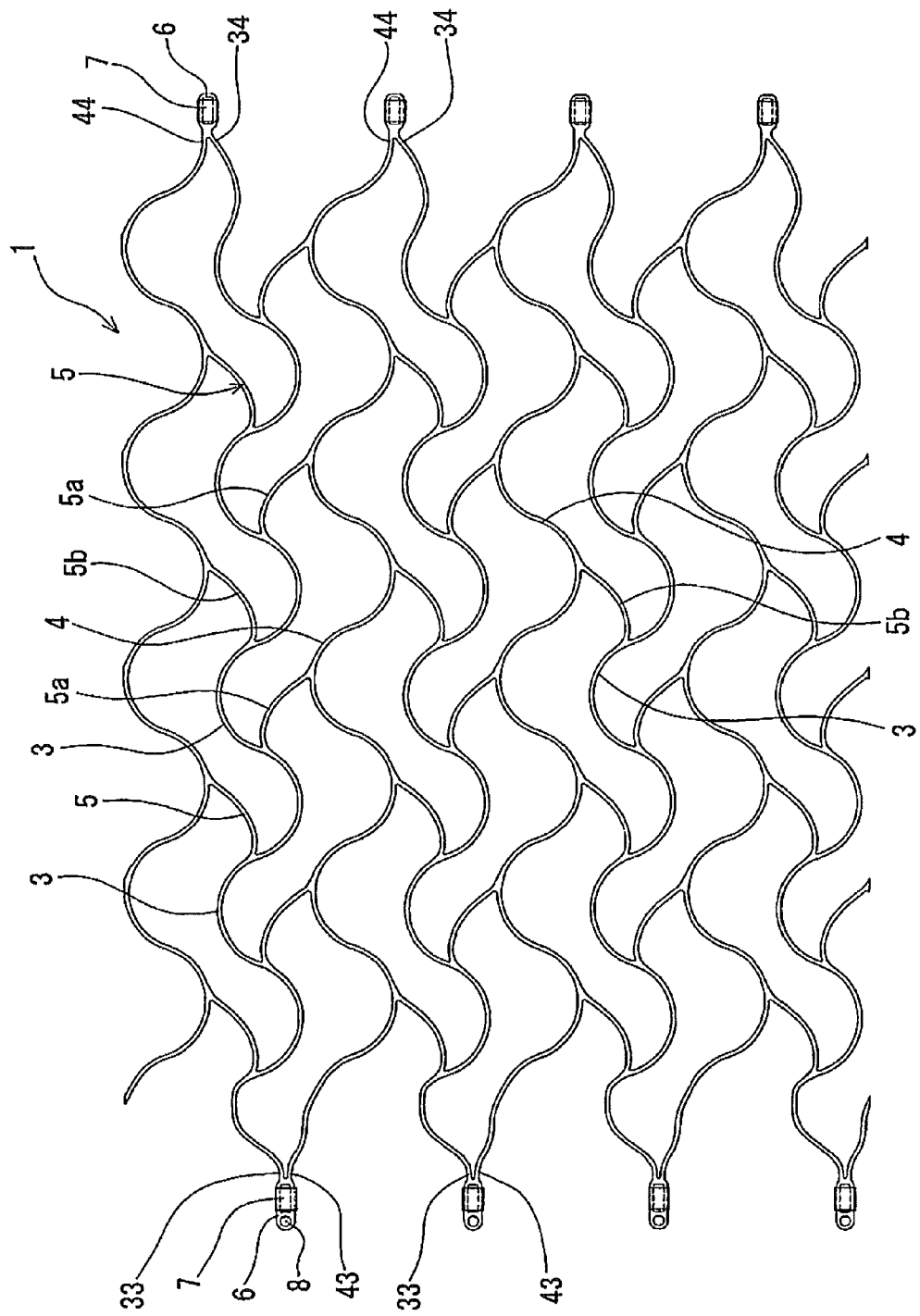
FIG. 6 is a development view of the stent of FIG. 1, in a maximally expanded state.

In addition, the stent 1 in this embodiment is manufactured in the state shown in FIG. 3 from a metallic pipe, is expanded into the state shown in FIGS. 5 and 6, and is thereafter heat treated. Therefore, the form shown in FIGS. 5 and 6 is the form or configuration of the stent in a maximally expanded state. This stent is inserted into a living body in the compressed state shown in FIG. 1. When the stent is inserted into a living body and is released from the compression, the stent takes a form transferred somewhat from the state shown in FIG. 3 to the state shown in FIGS. 5 and 6, but it substantially retains the form shown in FIG. 3. Hereafter, the form of the stent 1 in this embodiment will be described using the state shown in FIG. 3.

Figure 2:
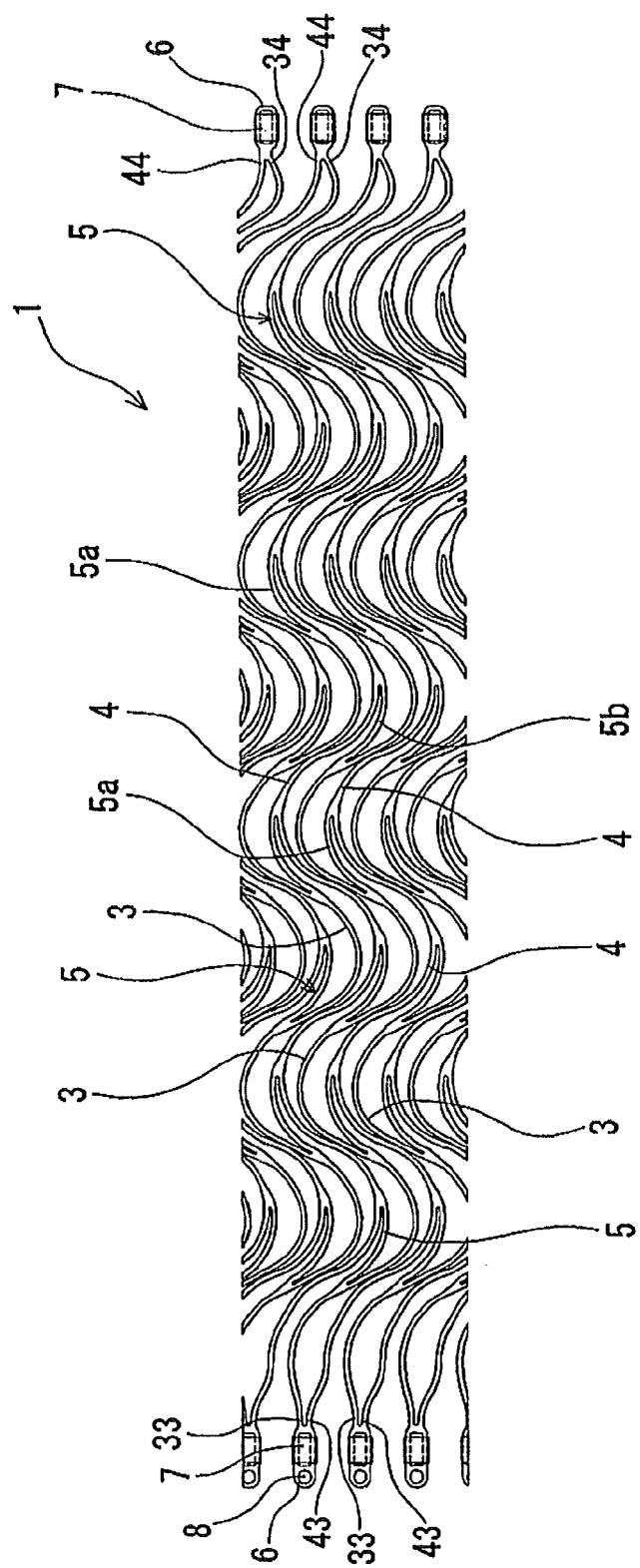
FIG. 2 is a development view of the stent of FIG. 1.

As shown in FIGS. 1-3, the stent 1 in this embodiment includes a plurality of first wave-shaped struts 3 extending in the axial direction of the stent from one end to the other end of the stent 1 and arranged in the circumferential direction of the stent; a plurality of second wave-shaped struts 4 similarly extending in the axial direction of the stent from one end to the other end of the stent and arranged in the circumferential direction of the stent; and a plurality of connecting struts 5 each interconnecting circumferentially adjacent ones of the first and second wave-shaped struts 3, 4, with the connecting struts 5 extending in the axial direction over a predetermined length.

The first wave-shaped struts 3 extend in the axial direction substantially parallel to the center axis of the stent. A plurality of the first wave-shaped struts 3 are arranged in the circumferential direction of the stent. The number of first wave-shaped struts 3 is preferably three or more, particularly about three to eight. Further, the plurality of the first wave-shaped struts 3 each are substantially at an equal angle to the center axis of the stent. That is, the first wave-shaped struts 3 are preferably circumferentially spaced apart from one another at equal angular intervals.

In the stent 1 in this embodiment, the first wave-shaped struts 3 each have the same waveform (inclusive of substantially the same waveform) continuing over a predetermined length, exclusive of both end portions. Specifically, each first wave-shaped strut 3 has a wave of the same waveform, more specifically the same wavelength and the same amplitude, continuing along the length of the strut 3, exclusive of portions near both end portions joined to the joint sections 6. In the case where the first wave-shaped strut 3 has the same waveform over its length (except for both end portions), the wavelength is preferably about 0.5 to 8.0 mm, particularly about 2.0 to 4.0 mm, and the amplitude is preferably about 0.5 to 10.0 mm, particularly about 1.0 to 3.0 mm, though depending on the outside diameter of the stent.

The second wave-shaped struts 4 also extend in the axial direction substantially in parallel to the center axis of the stent. A plurality of the second wave-shaped struts 4 are arranged in the circumferential direction of the stent, and each of the second wave-shaped struts 4 is disposed between the first wave-shaped struts. The number of second wave-shaped struts 4 is preferably three or more, particularly about three to eight. Further, the plurality of the second wave-shaped struts 4 are preferably so arranged that they are substantially at an equal angle to the center axis of the stent. That is, the second wave-shaped struts 4 are preferably circumferentially spaced apart from one another at equal angular intervals. In addition, the number of the second wave-shaped struts 4 is the same as the number of the first wave-shaped struts 3.

In the stent 1 in this embodiment, the second wave-shaped struts 4 each have the same waveform (inclusive of substantially the same waveform) continuing over a predetermined length, exclusive of both end portions. Specifically, the second wave-shaped strut 4 has a wave of the same waveform, more specifically the same wavelength and the same amplitude, continuing along the length of the strut 4, except for portions near both end portions joined to the joint sections 6. In the case where the second wave-shaped strut 4 has the same waveform over its length (except for both end portions), the wavelength is preferably about 0.5 to 8.0 mm, particularly about 2.0 to 4.0 mm, and the amplitude is preferably about 0.5 to 10.0 mm, particularly about 1.0 to 3.0 mm, though depending on the outside diameter of the stent.

Further, in the stent 1 in this embodiment, the first wave-shaped struts 3 and the second wave-shaped struts 4 possess a common waveform (inclusive of a substantially common waveform). Specifically, in the stent 1 in this embodiment, the first wave-shaped struts 3 and the second wave-shaped struts 4 have a common wavelength and a common amplitude.

In addition, the apexes 41 projecting to one side in the circumferential direction of the stent of the second wave-shaped strut 4 are shifted a predetermined distance in the axial direction of the stent relative to those apexes (apexes projecting to one side in the circumferential direction) 31 of the first wave-shaped strut 3 which are close (axially closest) to the apexes 41 in the circumferential direction of the stent 1 and which are curved in the same direction as the apexes 41. Similarly, the apexes 42 projecting to the other side (an opposite side) in the circumferential direction of the stent of the second wave-shaped strut 4 are shifted a predetermined distance in the axial direction of the stent relative to those apexes (apexes projecting to the other side (an opposite side) in the circumferential direction) 32 of the first wave-shaped strut 3 which are close (axially closest) to the apex 42 in the circumferential direction of the stent and which are curved in the same direction as the apexes 42.

In the stent in this embodiment, as above-mentioned, the first wave-shaped struts 3 and the second wave-shaped struts 4 have a common waveform. In this case, the second wave-shaped struts 4 are so formed that their phase is shifted a predetermined amount (predetermined distance) in the axial direction of the stent relative to the first wave-shaped struts 3, so that the apex positions do not overlap in the axial direction. In other words, the apexes 31 of the first wave-shaped struts 3 and the apexes 41 of the second wave-shaped struts 4 are not located on the same annular lines. In other words, those apexes 31, 41 of the wave-shaped struts which are adjacent to one another in the circumferential direction are located in a zigzag manner.

Figure 4:
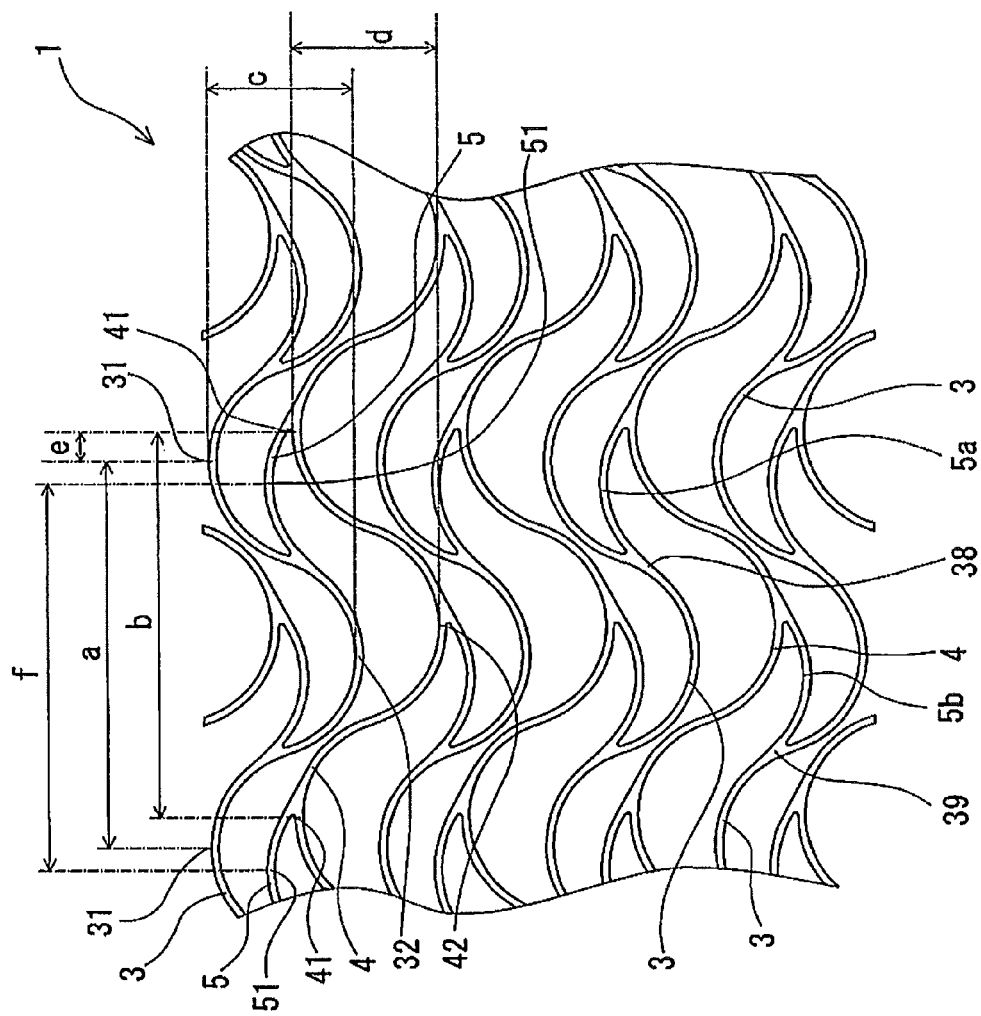
FIG. 4 is an enlarged view of a part of the stent shown in FIG. 3.

Specifically, as shown in FIG. 4, the first wave-shaped struts 3 are each in the shape of a sine wave having a wavelength a and an amplitude c. The wavelength a is preferably about 0.5 to 8.0 mm, particularly 2.0 to 4.0 mm. The length of the amplitude c is preferably about 0.5 to 10.0 mm, particularly 1.0 to 3.0 mm. The number of apexes of the wave of each of the first wave-shaped struts 3 (the total number of the apexes extending to one side and the other side in the circumferential direction) is preferably 1 to 100, particularly 1 to 80 (i.e., each first wave-shaped strut 3 includes 1 to 100 apexes). Similarly, the second wave-shaped struts 4 are each in the shape of a sine wave having a wavelength b and an amplitude d. The wavelength b is the same as the wavelength a, and the amplitude d is the same as the amplitude c. In addition, the number of apexes of the second wave-shaped strut 4 is the same as the number of the apexes of the first wave-shaped strut 3. The first wave-shaped strut 3 and the second wave-shaped strut 4 are so formed that their waveforms are deformed in the vicinity of their both end portions. Especially, at both end portions of the second wave-shaped strut 4, the waveform is relatively largely deformed. The axial-direction spacing e between the apex 31 of the first wave-shaped strut 3 and that apex 41 of the second wave-shaped strut 4 which is close to the apex 31 in the circumferential direction is preferably about 0.1 to 4.0 mm, particularly 0.1 to 2.0 mm. In the stent in this embodiment, since the first wave-shaped struts 3 and the second wave-shaped struts 4 have a common waveform, the axial-direction spacing e is the predetermined amount of mutual shift of their phases in the axial direction.

In addition, in the stent 1 in this embodiment, the apex 31 (the apex extending to one side in the circumferential direction of the stent) of the first wave-shaped strut 3 enters into (is positioned in) a space area (a trough) formed between adjacent (axially successive) apexes 42 and 42 (between those two apexes 42 of the second wave-shaped strut 4 which extend to the other side in the circumferential direction of the stent) of the second wave-shaped strut 4 adjacent to the first wave-shaped strut 3. Similarly, the apex 32 (the apex extending to the other side in the circumferential direction of the stent) of the first wave-shaped strut 3 enters into (is positioned in) a space area (a trough) formed between the adjacent (axially successive) apexes 41 and 41 (between those two apexes 41 of the second wave-shaped strut 4 which extend to one side in the circumferential direction of the stent) of the second wave-shaped strut 4 adjacent to the first wave-shaped strut 3.

Furthermore, in the stent 1 in this embodiment, the apex 41 (the apex extending to one side in the circumferential direction of the stent) of the second wave-shaped strut 4 enters into (is positioned in) a space area (a trough) formed between the adjacent (axially successive) apexes 32 and 32 (between those two apexes 32 of the first wave-shaped strut 3 which extend to the other side in the circumferential direction of the stent) of the first wave-shaped strut 3 adjacent to the second wave-shaped strut 4. Similarly, the apex 42 (the apex extending to the other side in the circumferential direction of the stent) of the second wave-shaped strut 3 enters into (is positioned in) a space area (a trough) formed between the adjacent (axially successive) apexes 31 and 31 (between those two apexes 31 of the first wave-shaped strut 3 which extend to one side in the circumferential direction of the stent) of the first wave-shaped strut 3 adjacent to the second wave-shaped strut 4.

Since the stent 1 in this embodiment has the above-mentioned configuration, the first wave-shaped struts and the second wave-shaped struts are in such a state that their apex portions mutually enter into each other, and, therefore, the stent 1 has a sufficient expansion maintaining force.

In addition, the stent 1 has one or more connecting struts 5 each of which interconnects one of the first wave-shaped struts 3 and the circumferentially adjacent second wave-shaped strut 4 and each of which extends in the axial direction over a predetermined length.

Particularly, in the stent 1 in this embodiment, the connecting strut 5 has one end near an inflection point of the wave-shaped strut on one side, has the other end (an opposite end) in a region ranging from a position near an apex of that wave-shaped strut on the other side which is adjacent to the wave-shaped strut on one side to a position slightly beyond the apex, extends in the axial direction, and is curved in the same direction as an apex of the wave-shaped strut on the other side. Specifically, as shown in FIG. 4, the connecting struts 5 are composed of first connecting struts 5a which have apexes directed to one side in the circumferential direction of the stent 1 and are curved, and second connecting struts 5b which have apexes directed to the other side in the circumferential direction of the stent 1 and are curved. The first connecting strut 5a has one end near a first inflection point 38 extending to one side in the circumferential direction of the first wave-shaped strut 3, has the other end in a region ranging from a position near an apex 41 of the second wave-shaped strut 4 adjacent thereto to a position slightly beyond the apex 41, extends in the axial direction, and is curved in the same direction as the apex 41 of the second wave-shaped strut 4. Similarly, the second connecting strut 5b has one end near a second inflection point 39 extending to the other side in the circumferential direction of the first wave-shaped strut 3, has the other end in a region ranging from a position near an apex 42 of the second wave-shaped strut 4 adjacent thereto to a position slightly beyond the apex 42, extends in the axial direction, and is curved in the same direction as the apex 42 of the second wave-shaped strut 4.

In the stent 1 in this embodiment, a plurality of the connecting struts 5 are provided in the axial direction and the circumferential direction of the stent. The connecting struts 5 are preferably provided in plurality and in series in the axial direction of the stent 1. The connecting struts 5 are preferably provided in plurality in the circumferential direction of the stent 1. Particularly, in the stent 1 in this embodiment, the first connecting struts 5a and the second connecting struts 5b are arranged alternately in the axial direction of the stent 1 and substantially on a straight line. In addition, regarding the circumferential direction of the stent 1, annular regions in each of which the first connecting struts 5a are arranged annularly and annular regions in each of which the second connecting struts 5b are arranged annularly are arranged alternately in the axial direction of the stent.

The connecting strut 5 is curved in a circular arc shape, and has a radius or radius of curvature equal to (inclusive of approximately equal to) the radius or radius of curvature of the circular arc shape of a curved part of the circumferentially adjacent first wave-shaped strut 3 or second wave-shaped strut 4. Specifically, the first connecting strut 5a is curved with a curvature equaling the curvature near the apex 31 of the first wave-shaped strut 3 and near the apex 41 of the second wave-shaped strut 4. Similarly, the second connecting strut 5b is curved with a curvature equaling the curvature near the apex 32 of the first wave-shaped strut 3 and near the apex 42 of the second wave-shaped strut 4. In addition, in the stent 1 in this embodiment, the distance f between the first connecting struts 5a adjacent to each other in the axial direction of the stent is equal to (inclusive of approximately equal to) the wavelength a of the first wave-shaped struts 3 and the wavelength b of the second wave-shaped struts 4. In this embodiment, the connecting struts 5a and 5b are close to each other in the circumferential direction, and the connecting struts 5a and 5b thus close to each other in the circumferential direction are different from each other in the curving direction. In addition, as above-mentioned, the connecting struts 5a are arranged on a straight line in the axial direction, and the connecting struts 5a close to each other in the axial direction are the same in the curving direction. Similarly, the connecting struts 5b are also arranged on a straight line in the axial direction, and the connecting struts 5b close to each other in the axial direction are the same in the curving direction.

The stent 1 in this embodiment has multiple connecting struts 5 by which a portion near every one of the inflection points of the wave-shaped strut on one side and a region ranging from every one of the apexes of that wave-shaped strut on the other side which is adjacent to the wave-shaped strut on one side to a position slightly beyond the apex are interconnected. While each connecting strut 5 preferably has one end near an inflection point of the wave-shaped strut on one side as above-mentioned, the position of one end is not limited to this region, and it suffices for one end to be located at a part not near the apex of the wave-shaped strut on one side. In addition, while the other end of the connecting strut is preferably located at a part slightly beyond the apex of the wave-shaped strut on the other side, it may be located at the apex of the wave-shaped strut.

The stent 1 in this embodiment includes the joint sections 6 by which the end portion at one end of each first wave-shaped strut 3 is joined to the end portion at one end of one of the circumferentially adjacent second wave-shaped struts 4, and the end portion at the other end (an opposite end) of each first wave-shaped strut 3 is joined to the end portion at the other end (an opposite end) of one of the circumferentially adjacent second wave-shaped struts 4. Similarly, the end portion at one end of each second wave-shaped strut 4 is joined to the end portion at one end of one of the circumferentially adjacent first wave-shaped struts 3, and the end portion at the other end (an opposite end) of each second wave-shaped strut 4 is joined to the end portion at the other end (an opposite end) of one of the circumferentially adjacent first wave-shaped struts 3. Specifically, one end portion 34 of the first wave-shaped strut 3 of the stent 1 is joined to one end portion 44 of the second wave-shaped strut 4 which is on one circumferential side of the first wave-shaped strut 3 by the joint section 6. In addition, the other end portion 33 of the first wave-shaped strut is joined to the other end portion 43 of the second wave-shaped strut 4 on the other circumferential side of the first wave-shaped strut by the joint section 6. In other words, the joint sections 6 on one end of the stent and the joint sections 6 on the other end of the stent are different from each other in combination of the first wave-shaped strut 3 and the second wave-shaped strut 4 which are joined to each other. The joint sections 6 on one end of the stent and the joint sections 6 on the other end of the stent are circumferentially shifted relative to each other such that the joint sections at both ends of the stent are not arranged in straight lines parallel to the central axis of the stent.

Figure 7:
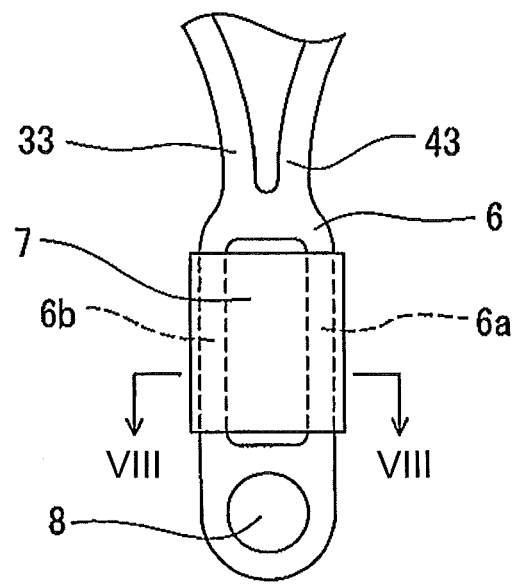
FIG. 7 is an enlarged view of a joint section of the stent shown in FIG. 1.
Figure 8:
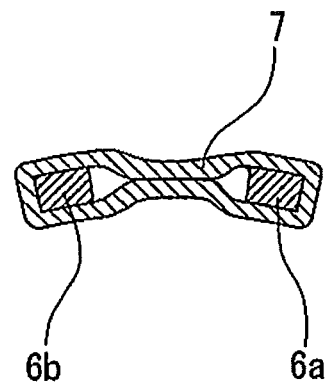
FIG. 8 is an enlarged cross-sectional view taken along the section line VIII-VIII in FIG. 6.

The joint sections 6 are each fitted with a radiopaque marker 7, as shown in FIGS. 3 and 7. In this embodiment, the joint section 6 is comprised of two frame parts 6a, 6b extending parallel to each other with a predetermined spacing between the two frame parts 6a, 6b, and the radiopaque marker 7 envelopes the two frame parts 6a, 6b partly or entirely (inclusive of substantially entirely). The radiopaque marker 7 is in the shape of a thin-walled rectangular parallelepiped, accommodates the two frame parts 6a, 6b, and is recessed in a central area so as to be fixed to the two frame parts 6a, 6b. Examples of the material which can be suitably used to form the radiopaque marker include one (elemental substance) or two or more (alloy) selected from the group consisting of iridium, platinum, gold, rhenium, tungsten, palladium, rhodium, tantalum, silver, ruthenium, and hafnium. In addition, the length of the marker is preferably about 0.1 to 4.0 mm, particularly 0.3 to 1.0 mm. The material thickness of the marker is preferably 0.01 to 0.30 mm, particularly 0.03 to 0.10 mm. In addition, the joint sections 6 on one end of the stent are each formed with an engaging hole 8. The diameter of the engaging hole 8 is preferably about 0.01 to 0.30 mm, particularly 0.05 to 0.20 mm.

In the stent 1 in this embodiment, the one end portions 34, 44 of the struts constitute the distal end of the stent so that the one end portions 34, 44 of the struts are at the distal end of the stent. The other end portions 33, 43 of the struts provided with the respective engaging hole or through opening 8 constitute the proximal end of the stent so that the other end portions 34, 44 of the struts are at the proximal end of the stent.

Figure 9:
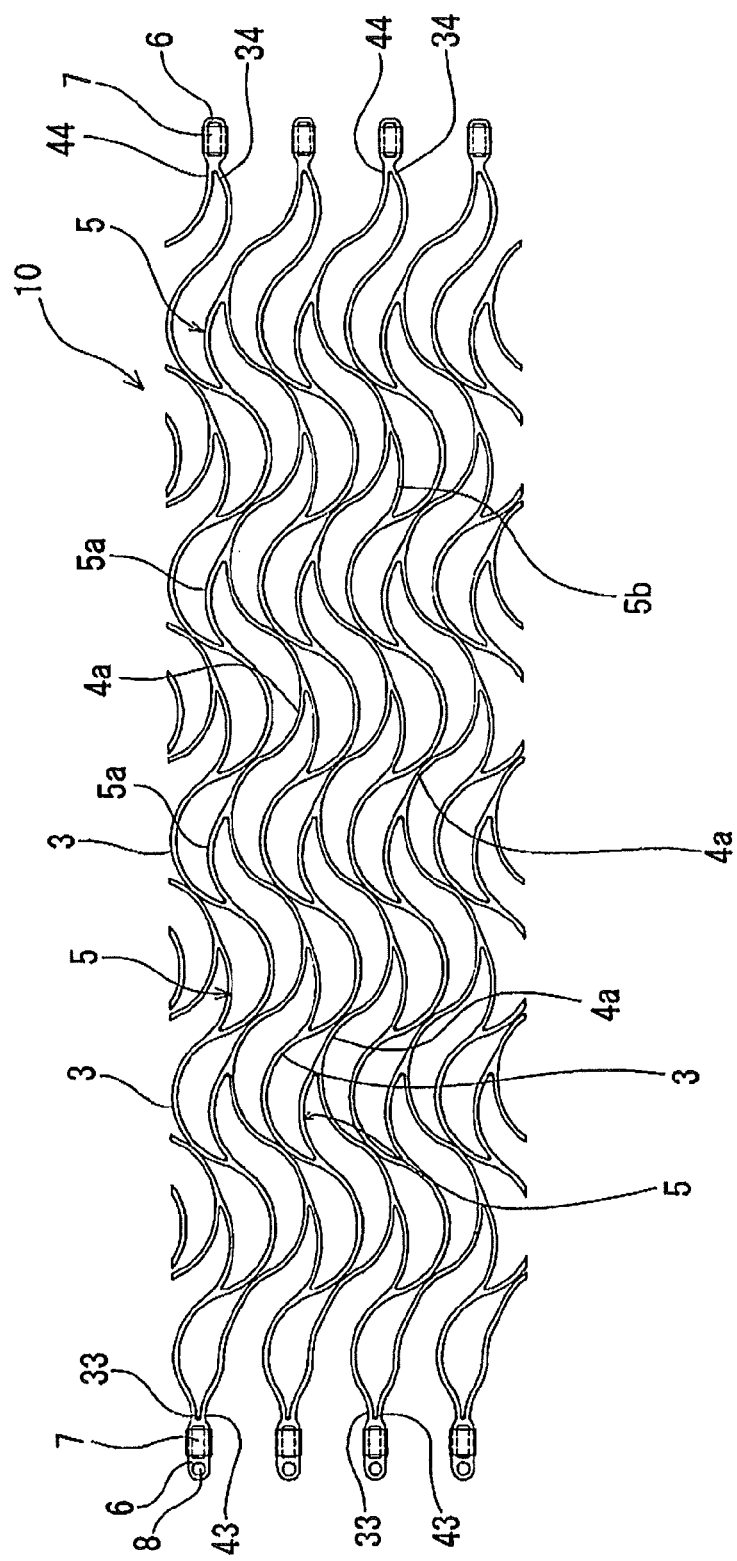
FIG. 9 is a development view, at the time of manufacturing, of a stent for placement in living body according to another embodiment disclosed here.
Figure 10:
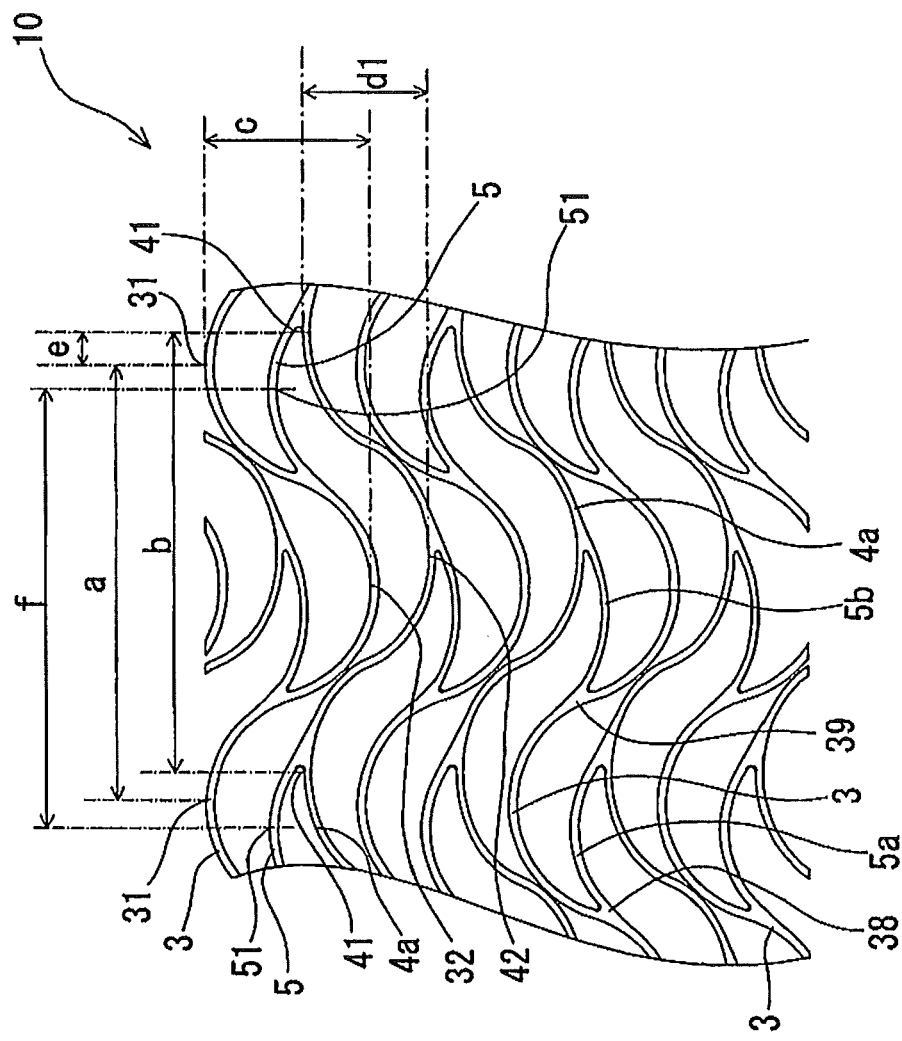
FIG. 10 is an enlarged view of a part of the stent shown in FIG. 9.

In addition, the form of the stent may be the form of the stent 10 shown in FIGS. 9 and 10 which illustrate a stent for placement in living body according to another embodiment disclosed here. This stent 10 differs from the above-described stent 1 only in the waveform of the second wave-shaped strut. In a manner similar to that described above, the stent 10 is configured so that the apexes 41, 42 of the second wave-shaped strut 4a are shifted a predetermined distance in the axial direction of the stent relative to those apexes 31, 32 of the first wave-shaped strut 3 which are located close to the apex 41, 42 in the circumferential direction of the stent 10 and which are curved in the same direction as the apexes 41, 42.

In the stent 10 in this embodiment, the first wave-shaped strut 3 and the second wave-shaped strut 4a possess different waveforms. Specifically, the second wave-shaped strut 4a has an amplitude different from the amplitude of the first wave-shaped strut 3, though the first wave-shaped strut 3 and the second wave-shaped strut 4a possess a common (inclusive of substantially common) wavelength.

Specifically, as shown in FIG. 10, the second wave-shaped struts 4a are in the shape of a sine wave having a wavelength b and an amplitude d1. The amplitude d1 is different from the amplitude c of the stent 1. In this example, the amplitude d1 of the second wave-shaped struts 4a is smaller than the amplitude c of the first wave-shaped struts 3. The wavelength b of the second wave-shaped struts 4a is the same as the wavelength a of the first wave-shaped struts 3. The amplitude d1 of the second wave-shaped struts 4a may be greater than the amplitude c of the first wave-shaped struts 3.

Figure 11:
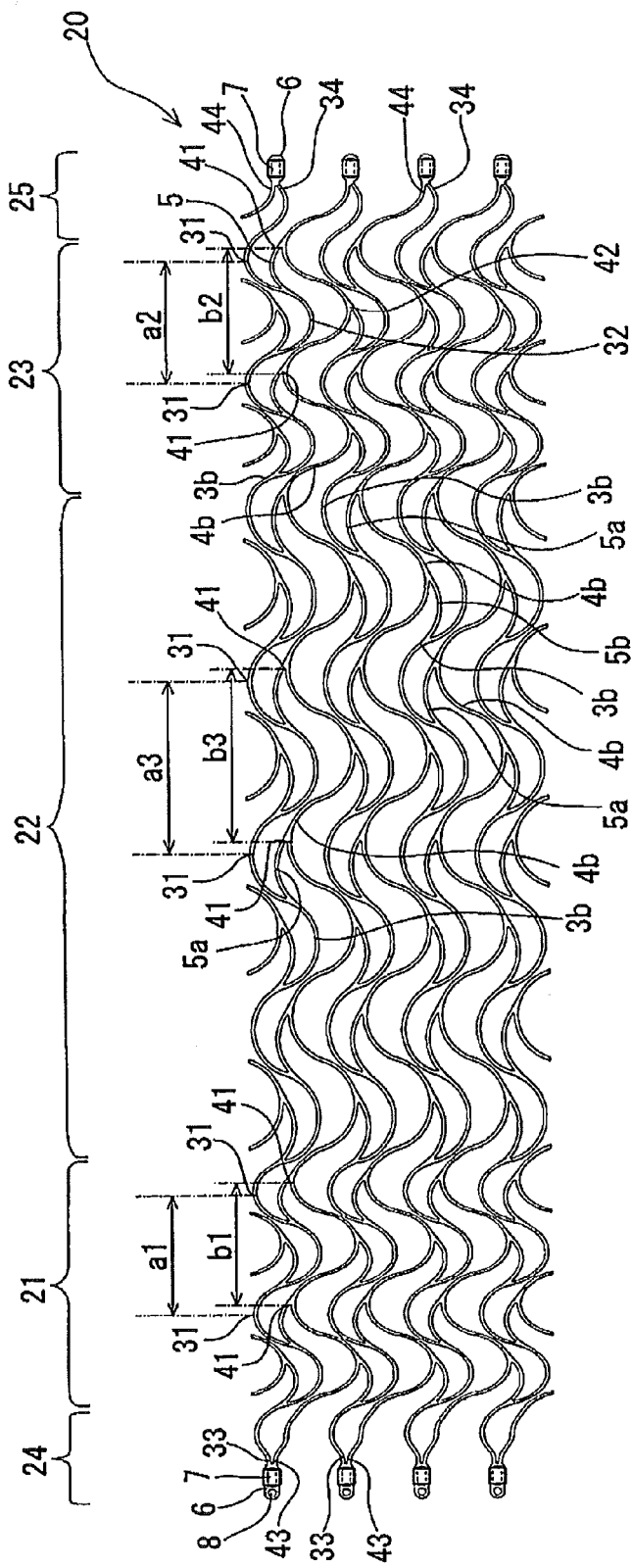
FIG. 11 is a development view, at the time of manufacturing, of a stent for placement in living body according a further embodiment.

The stent may also be of the form shown in FIG. 11 which illustrates a stent 30 for placement in living body according to a further embodiment. This stent 20 differs from the above-described stent 1 in the waveforms of the first wave-shaped struts and the second wave-shaped struts. The stent 20 in this embodiment is once again configured so that the apexes 41, 42 of the second wave-shaped strut 4b are shifted a predetermined distance in the axial direction of the stent relative to those apexes 31, 32 of the first wave-shaped strut 3b which are located close to the apexes 41, 42 in the circumferential direction of the stent 20 and which are curved in the same direction as the apexes 41, 42.

As shown in FIG. 10, the waveform at both side portions 21, 23 of the stent is different from the waveform at a central portion 22 of the stent. Specifically, in the first wave-shaped strut 3b, one side portion 21 and the other side portion 23 (an opposite side portion) have the same (inclusive of substantially the same) waveform continuing over a predetermined length, namely have a waveform with the same wavelength and the same amplitude, whereas the central portion 22 is greater in wavelength than the both side portions 21, 23. The amplitude of the first wave-shaped strut 3b is the same (inclusive of substantially the same) over its entire length, exclusive of both end portions 24, 25. Specifically, the wavelength a1 and the wavelength a2 at both side portions 21, 23 are substantially the same; in addition, the wavelength a1 and the wavelength a2 at both side portions 21 and 23 are smaller than the wavelength a3 at the central portion 22.

As shown in FIG. 10, the waveform at both side portions 21, 23 is different from the waveform at a central portion 22. Specifically, in the second wave-shaped strut 4b, one side portion 21 and the other side portion 23 (an opposite end portion) have the same (inclusive of substantially the same) waveform continuing over a predetermined length. That is, the one side portion 21 and the other side portion 23 have a waveform with the same wavelength and the same amplitude along their lengths, whereas the central portion 22 is greater in wavelength than the both side portions 21, 23. The amplitude of the second wave-shaped strut 4b is the same (inclusive of substantially the same) along its entire length, exclusive of both end portions 24, 25. Specifically, the wavelength b1 and the wavelength b2 at both side portions 21, 23 are substantially the same; in addition, the wavelength b1 and the wavelength b2 at both side portions 21, 23 are smaller than the wavelength b3 at the central portion 22. In the stent 1 in this embodiment, the first wave-shaped strut 3b and the second wave-shaped strut 4b have a common (inclusive of substantially common) waveform, exclusive of the both end portions 24, 25.

The smaller wavelength at both side portions 21, 23 of the stent 20 than at the central portion 22 helps ensure that the expansion maintaining force at both end portions of the stent is relatively high.

In the above-described embodiment, while the wavelengths at both side portions 21, 23 of the stent are the same and are smaller than the wavelength at the central portion 22, such a pattern is not limitative. For example, there may be adopted a configuration in which the wavelengths at both side portions 21, 23 of the stent are different, or a configuration in which the wavelength at the central portion 22 of the stent is smaller than the wavelengths at both side portions 21, 23 of the stent. In addition, the amplitude of the second wave-shaped struts 4b may be different from the amplitude of the first wave-shaped struts 3b. Additionally, the first wave-shaped strut 3b and the second wave-shaped strut 4b may each be varied in amplitude at a part or parts thereof.

Figure 12:
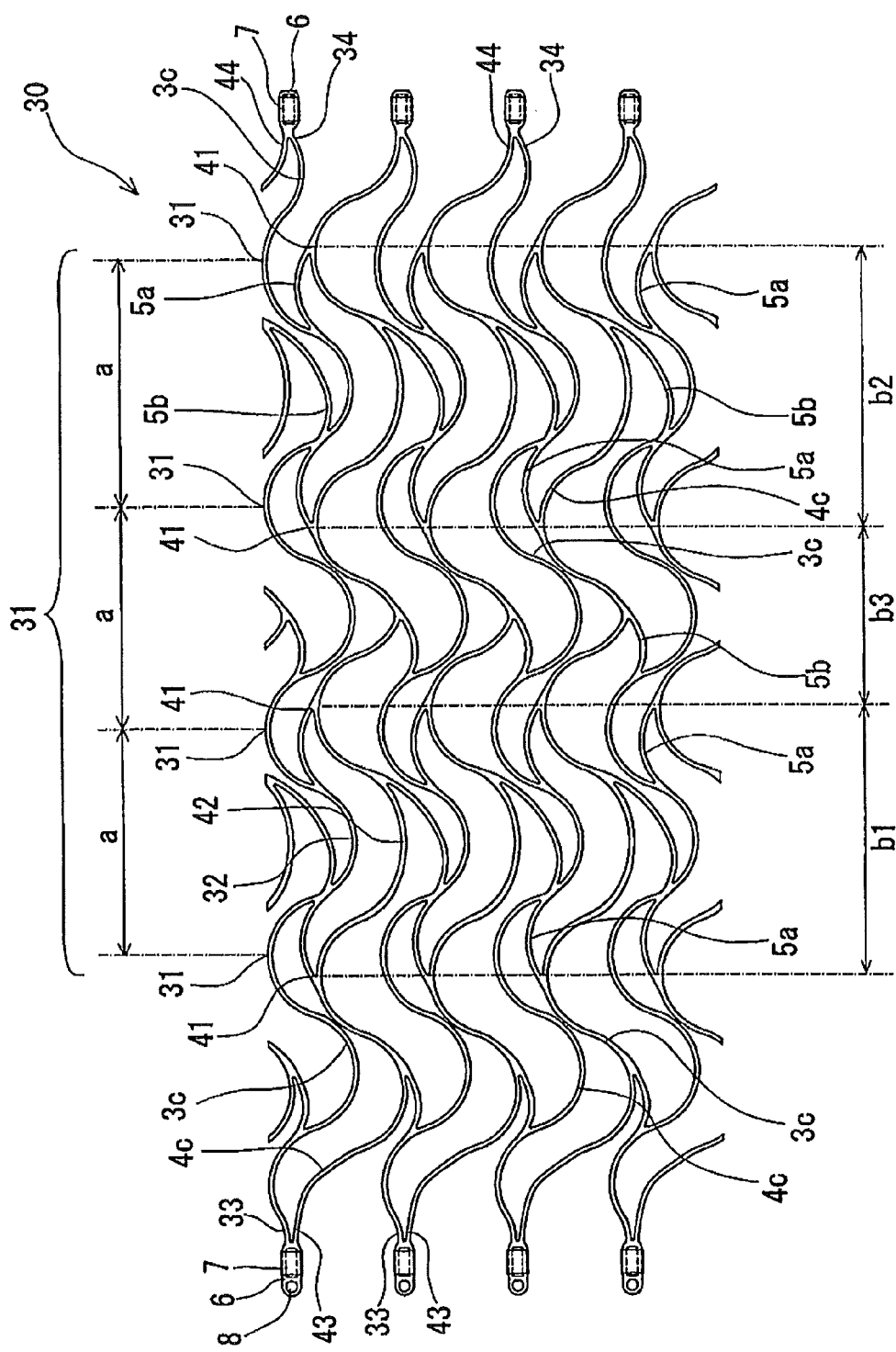
FIG. 12 is a development view, at the time of manufacturing, of a stent for placement in living body according to yet another embodiment.

The stent may also take the form shown in FIG. 12 which shows a stent 30 for placement in living body according to yet another embodiment. The stent 30 differs from the above-described stent 1 only in the waveform of the second wave-shaped strut.

As in other embodiments described above, in the stent 30 in this embodiment, the apexes 41, 42 of the second wave-shaped strut 4c are shifted a predetermined distance in the axial direction of the stent relative to those apexes 31, 32 of the first wave-shaped strut 3c which are located close to the apexes 41, 42 in the circumferential direction of the stent 1 and which are curved in the same direction as the apexes 41, 42.

In the stent 30 in this embodiment, the first wave-shaped strut 3c and the second wave-shaped strut 4c are different from each other in waveform. Specifically, the second wave-shaped strut 4c has its central portion 31 constituting a various part waveform. The first wave-shaped strut 3c has the same wavelength a which is repeated also at its central portion 31. On the other hand, the second wave-shaped strut 4c has a large wavelength b1 on one side of the central portion 31, a large wavelength b2 also on the other side of the central portion 31, and a comparatively smaller wavelength b3 on the central side (i.e., b3 is smaller than b1 and b2). In addition, in this stent, the first wave-shaped strut 3c is uniform in amplitude over its entire length, and the second wave-shaped strut 4c is also uniform in amplitude over its entire length. Further, the first wave-shaped strut 3c and the second wave-shaped strut 4c have a common amplitude (inclusive of substantially common).

In the stents in all the embodiments described above, a biologically active agent may be releasably contained in the stent. Methods for releasably containing a biologically active agent in the stent include, for example, a method in which a surface of the stent is coated with a polymer (e.g., a biodegradable polymer) which contains a biologically active agent.

The biodegradable polymer is not particularly limited insofar as it is decomposed in living bodies through an enzymatic or non-enzymatic process and the decomposed product is nontoxic. Examples of the biodegradable polymer which can be used here include polylactic acid, polyglycolic acid, polylactic acid-polyglycolic acid copolymer, polycaprolactone, polylactic acid-polycaprolactone copolymer, polyorthoesters, polyphosphazene, polyphosphoric acid ester, polyhydroxybutyric acid, polymaleic acid, poly-α-amino acids, collagen, gelatin, laminin, heparan sulfate, fibronectin, vitronectin, chondroitin sulfate, hyaluronic acid, polypeptide, chitin, chitosan, etc.

In addition, examples of the biologically active agent to be used here include agents capable of accelerating the liquefaction or metabolism of thrombus or thrombotic complex matter or agents capable of suppressing the increase of thrombus or thrombotic complex matter, agents for suppressing inner membrane hypertrophy, carcinostatic agents, immunosuppressor, antibiotic, antirheumatic, antithrombotic agents, HMG-CoA reductase inhibitor, ACE inhibitor, calcium antagonist, antilipemia agents, anti-inflammatory agents, integrins inhibitor, antiallergic agents, antioxidant, GP 11b111a antagonist, retinoid, flavonoids and carotenoids, lipid improver, DNA synthesis inhibitor, tyrosine kinase inhibitor, antiplatelet agents, vascular smooth muscle growth inhibitor, bio-derived materials, interferon, and epithelial cells produced by genetic engineering, etc. Mixtures of two or more of the just-mentioned agents may also be used.

The agents capable of accelerating the liquefaction or metabolism of thrombus or thrombotic complex matter or agents capable of suppressing the increase of thrombus or thrombotic complex matter are as follows. Examples of the agents capable of accelerating liquefaction of thrombus or thrombotic complex matter include streptokinase, plasminogen activator, urokinase, staphynokinase, lumbrokinase, nattokinase, and their analogs. Examples of the agents capable of suppressing the increase of thrombus or thrombotic complex matter include antiplatelet agents represented by acetylsalicylic acid, ticlopidine, dipyridamole, cilostazol, beraprost sodium, limaprost alfadex, ethyl icosapentate, sarpogrelate hydrochloride, trapidil, clopidogrel, prasugrel and their analogs, or anticoagulants represented by GP 11b/111a antagonist, heparin, and warfarin potassium.

Preferable examples of the carcinostatic agents include vincristin, vinblastin, vindesin, irinotecan, pirarubicin, paclitaxel, docetaxel, methotrexate, etc. Preferable examples of the immunosuppressor include sirolimus, tacrolimus, azathioprine, ciclosporin, cyclophosphamide, mycophenolate mofetil, gusperimus, mizorbin, etc. Preferable examples of the antibiotic include mitomycin, adriamycin, doxorubicin, actinomycin, daunorubicin, idarubicin, pirarubicin, aclarubicin, epirubicin, peplomycin, zinostatin stimalamer, etc. Preferable examples of the antirheumatic include methotrexate, sodium thiomalate, penicillamine, lobenzarit, etc. Preferable examples of the antithrombotic agents include heparin, aspirin, antithrombin preparation, ticlopidine, hirudin, etc. Preferable examples of the HMG-CoA reductase inhibitor include cerivastatin, cerivastatin sodium, atorvastatin, nisvastatin, itavastatin, fluvastatin, fluvastatin sodium, simvastatin, lovastatin, pravastatin, etc. Preferable examples of the ACE inhibitor include quinapril, perindopril erbumine, trandolapril, cilazapril, temocapril, delapril, enalapril maleate, lisinopril, captopril, etc. Preferable examples of the calcium antagonist include nifedipine, nilvadipine, diltiazem, benidipine, nisoldipine, etc. Preferable examples of the antilipemia agents include probucol. Preferable examples of the antiallergic agents include tranilast. Preferable examples of the retinoids include all-trans-retinoic acid. Preferable examples of the flavonoids and carotenoids include catechins, particularly, epigallocatechin gallate, anthocyanine, proanthocyanidin, lycopene, β-carotene, etc. Preferable examples of the tyrosine kinase inhibitors include genistein, tyrphostin, erbstatin, etc. Preferable examples of the anti-inflammatory agents include salicylic acid, aspirin, acetaminophen, phenacetin, indomethacin, diclofenac sodium, piroxicam, fenoprofen calcium, ibuprofen, chlorpheniramine maleate, diflunisal, dexamethasone, clobetasol propionate, diflorasone diacetate, difluprednate, betamethasone dipropionate, diflucortolone valeate, budesonide, fluocinonide, amcinonide, halcinonide, hydrocortisone butyrate dipropionate, mometasone furoate, betamethasone butyrate propionate, deprodone propionate, betamethasone valeate, beclometasone dipropionate, fluocinoloneacetonide, prednisolone valeate acetate, triamcinoloneacetonide, flumetasone pivalate, clobetasone butyrate, hydrocortisone butyrate, prednisolone acetate, methylprednisolone acetate, etc. Preferable examples of the bio-derived materials include EGF (epidermal growth factor), VEGF (vascular endothelial growth factor), HGF (hepatocyte growth factor), PDGF (platelet derived growth factor), bFGF (basic fibroblast growth factor), etc.

The stent of the type disclosed here is preferably a so-called self-expandable stent which is cylindrical in shape (inclusive of substantially cylindrical in shape), compressed toward its center axis at the time of insertion into a living body, and automatically outwardly expandable when placed (put indwelling) in the living body, thereby being restored into its pre-compression shape. All embodiments of the stent described above can be a self-expandable stent.

The material constituting the self-expandable stent is preferably a superelastic metal. As the superelastic metal, superelastic alloys are preferably used. The superelastic alloys here means those alloys which are generally called shape memory alloys and which show superelasticity at least at a living body temperature (around 37° C.). Particularly preferable for use here are superelastic metal bodies such as Ti—Ni alloys containing 49 to 53 atomic % of Ni, Cu—Zn alloys containing 38.5 to 41.5 wt % of Zn, Cu—Zn—X alloys (X=Be, Si, Sn, Al, Ga) containing 1 to 10 wt % of X, Ni—Al alloys containing 36 to 38 atomic % of Al, etc. Especially preferred are the above-mentioned Ti—Ni alloys. Use of Ti—Ni—X alloys (X=Co, Fe, Mn, Cr, V, Al, Nb, W, B or the like) prepared by replacing part of the Ti—Ni alloys by 0.01 to 10.0% of X, use of Ti—Ni—X alloys (X=Cu, Pb, Zr) prepared by replacing part of the Ti—Ni alloys by 0.01 to 30.0% of atoms, or selection of cold working ratio and/or final heat treatment conditions, may be made, whereby mechanical properties of the superelastic alloy can be changed, as required. While using the above-mentioned Ti—Ni—X alloy, the cold working ratio and/or final heat treatment conditions may be selected, whereby the mechanical properties of the alloy can be changed, as required. Of the superelastic alloy to be used, the buckling strength (the yield stress under load) is 5 to 200 kg/mm2 (22° C.), preferably 8 to 150 kg/mm2, and the restoring stress (the yield stress when unloaded) is 3 to 180 kg/mm2 (22° C.), preferably 5 to 130 kg/mm2. The superelasticity here means a property of a metal such that even upon deformation (bending, extension, compression) of the metal into a region where ordinary metals undergo plastic deformation at use temperature, the deformed metal is restored substantially into its pre-compression shape after release of the deformation, without needing heating.

In the stents in all the embodiments described above, the diameter of the stent in a non-expanded state (i.e., in a compressed state) is preferably about 0.5 to 1.8 mm, particularly 0.6 to 1.4 mm. In addition, the length of the stent in a non-expanded state (i.e., in a non-compressed state) is preferably about 5 to 200 mm, particularly 8.0 to 100.0 mm. In addition, the diameter of the stent upon forming (before compression) is preferably about 1.5 to 6.0 mm, more preferably 2.0 to 5.0 mm. Further, the material thickness of the stent is preferably about 0.05 to 0.15 mm, particularly 0.05 to 0.40 mm. The width of the wave-shaped struts is preferably 0.01 to 1.00 mm, particularly 0.05 to 0.2 mm. Surfaces of the wave-shaped struts are preferably in the state of having been processed to be smooth; in this case, smoothening is preferably carried out by electropolishing. The strength of the stent in the radial direction is preferably 0.1 to 30.0 N/cm, particularly 0.5 to 5.0 N/cm.

In addition, the stent described here may also be a balloon-expandable stent which is cylindrical in shape (inclusive of substantially cylindrical), has a diameter for insertion into a lumen in a living body, and is expanded when a radially outwardly directed spreading force is exerted on the stent from the inside of the stent. All embodiments of the stent described above can be a balloon-expandable stent.

The material forming the stent in the case of the balloon-expandable stent is preferably a material which has a certain degree of bio-compatibility. The material forming the stent may be, for example, stainless steel, tantalum or tantalum alloy, platinum or platinum alloy, gold or gold alloy, cobalt-based alloy, etc. After the material is formed into a stent shape, it may be plated with a noble metal (gold, platinum). As the stainless steel, preferred is SUS316L, which is the highest in corrosion resistance.

In addition, as the material for forming the stent in the case of the balloon-expandable stent, bio-degradable metals may also be used. The bio-degradable metal which can be used is, for example, pure magnesium or magnesium alloy, calcium, zinc, lithium, etc. Pure magnesium or magnesium alloy is preferably used. As the magnesium alloy, preferred are those which contain magnesium as a principal ingredient and contain at least one element selected from the bio-compatible element group of Zr, Y, Ti, Ta, Nd, Nb, Zn, Ca, Al, Li, and Mn.

Examples of the magnesium alloy include those which contain 50 to 98% of magnesium, 0 to 40% of lithium (Li), 0 to 5% of iron, and 0 to 5% of other metals or rare earth elements (cerium, lanthanum, neodymium, praseodymium, etc.). Other examples of the magnesium alloy include those which contain 79 to 97% of magnesium, 2 to 5% of aluminum, 0 to 12% of lithium (Li), and 1 to 4% of rare earth elements (cerium, lanthanum, neodymium, praseodymium, etc.). Further examples of the magnesium alloy include those which contain 85 to 91% of magnesium, 2% of aluminum, 6 to 12% of lithium (Li), and 1% of rare earth elements (cerium, lanthanum, neodymium, praseodymium, etc.). Other examples of the magnesium alloy include those which contain 86 to 97% of magnesium, 2 to 4% of aluminum, 0 to 8% of lithium (Li), and 1 to 2% of rare earth elements (cerium, lanthanum, neodymium, praseodymium, etc.). Further examples of the magnesium alloy include those which contain 8.5 to 9.5% of aluminum, 0.15 to 0.4% of manganese (Mn), and 0.45 to 0.9% of zinc, the balance being magnesium. Other examples of the magnesium alloy include those which contain 4.5 to 5.3% of aluminum and 0.28 to 0.5% of manganese (Mn), the balance being magnesium. Further examples of the magnesium alloy include those which contain 55 to 65% of magnesium, 30 to 40% of lithium (Li), and 0 to 5% of other metals and/or rare earth elements (cerium, lanthanum, neodymium, praseodymium, etc.).

In addition, the stent is preferably chamfered. Methods for chamfering include a method in which after the stent is formed into the final shape, the stent is subjected to chemical polishing, electropolishing or mechanical polishing.

Further, after the final shape of the stent is produced, the stent is preferably annealed. As a result of the annealing, flexibility and plasticity of the stent as a whole are enhanced, and the property for placement (put indwelling) in a bent blood vessel is enhanced. The annealing helps ensure that, as compared with the case where annealing is not conducted, the force for restoration into the pre-expansion shape after expansion of the stent, particularly, the force for restoration into a rectilinear shape which is exhibited upon expansion of the stent in a bent blood vessel part, is reduced, so that the physical stimulus exerted on the inner wall of the bent blood vessel by the stent is reduced, whereby the cause of restenosis can be reduced. In order to inhibit or prevent formation of an oxide film on the stent surface, the annealing of the stent is preferably carried out by heating at a temperature of 900 to 1200° C. in an inert gas atmosphere (e.g., in a mixed gas of nitrogen and hydrogen), followed by rapid cooling.

Furthermore, in the stents in all the embodiments described above, processing to form minute grooves, holes or the like for accelerating stabilization of plaque, or deposition of protein, drug, gene or the like on the stent may be carried out.

EXAMPLES

Specific examples of the stent will now be described.

A nickel-titanium alloy pipe of 2.0 mm in diameter was cut according to the design shown in FIG. 3 by use of a YAG laser beam machining apparatus, to produce a stent substrate. After a deburring treatment, the stent substrate was expanded to a diameter of 4.5 mm, and was further subjected to heat setting (520° C., 15 min), to obtain a stent substrate having shape memory property and superelasticity. The stent substrate was further subjected to electropolishing, to produce a stent substrate in which the struts had a width of 0.07 mm and a material thickness of 0.07 mm, and stent engaging holes were 0.2 mm in diameter. Then, platinum-iridium alloy pipes of 0.32 mm in diameter, 0.05 mm in material thickness, and 0.4 mm in length were fixed to four joint sections at both ends of the stent substrate, as radiopaque markers, to produce a stent according to the present invention.

When the stent obtained as above was bent so as to make contact with an outer surface of a pipe of 10 mm in diameter, it was confirmed that the stent was bent while maintaining a uniform inside diameter and without kinking. In addition, the radial-direction strength of the stent was measured by a radial force testing machine, to be 1.2 N/cm. When a nylon suture of 0.1 mm in diameter was passed through the engaging holes of the stent, the stent end portions were contracted and then the nylon suture was released, it was confirmed that the stent returned into its original shape and that the nylon suture could be recovered without being caught by the engaging holes.

A stent delivery system is now described below, using an example shown in the drawings. The stent delivery system is, in other words, a living organ dilator.

Figure 13:
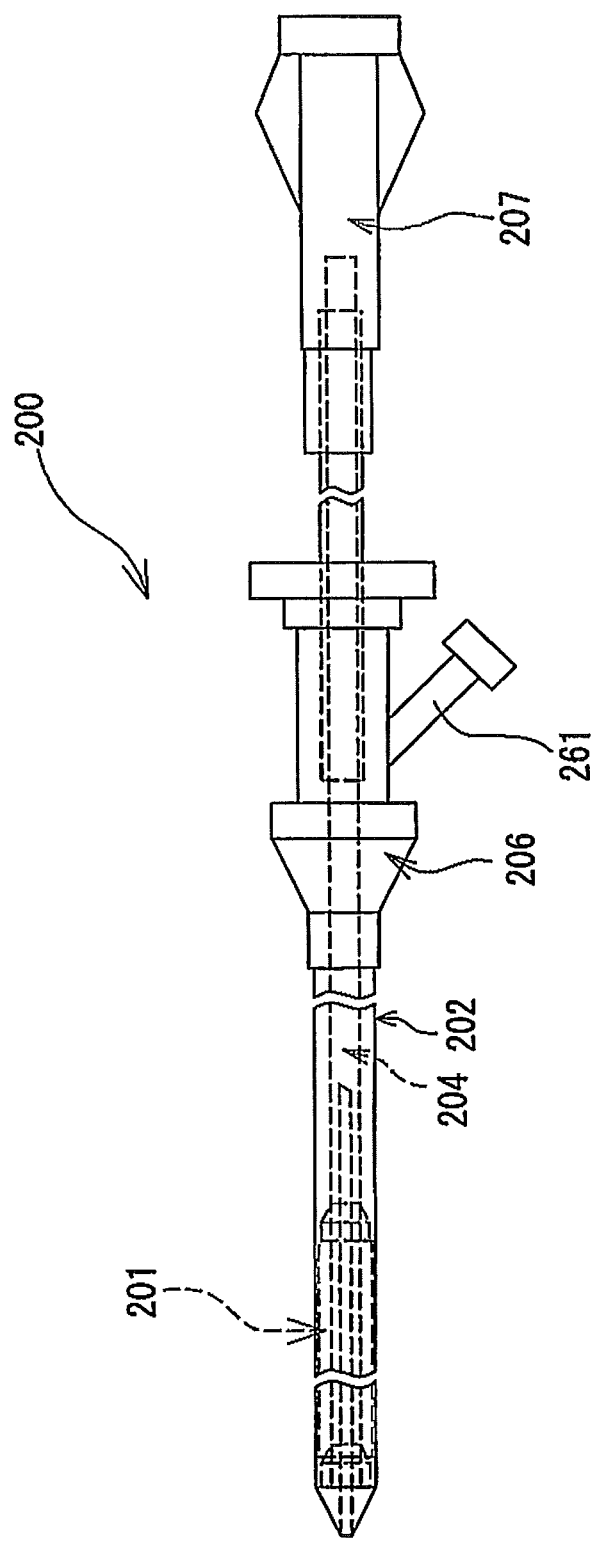
FIG. 13 is a partly omitted front view of a stent delivery system usable together with the stent disclosed here.
Figure 14:
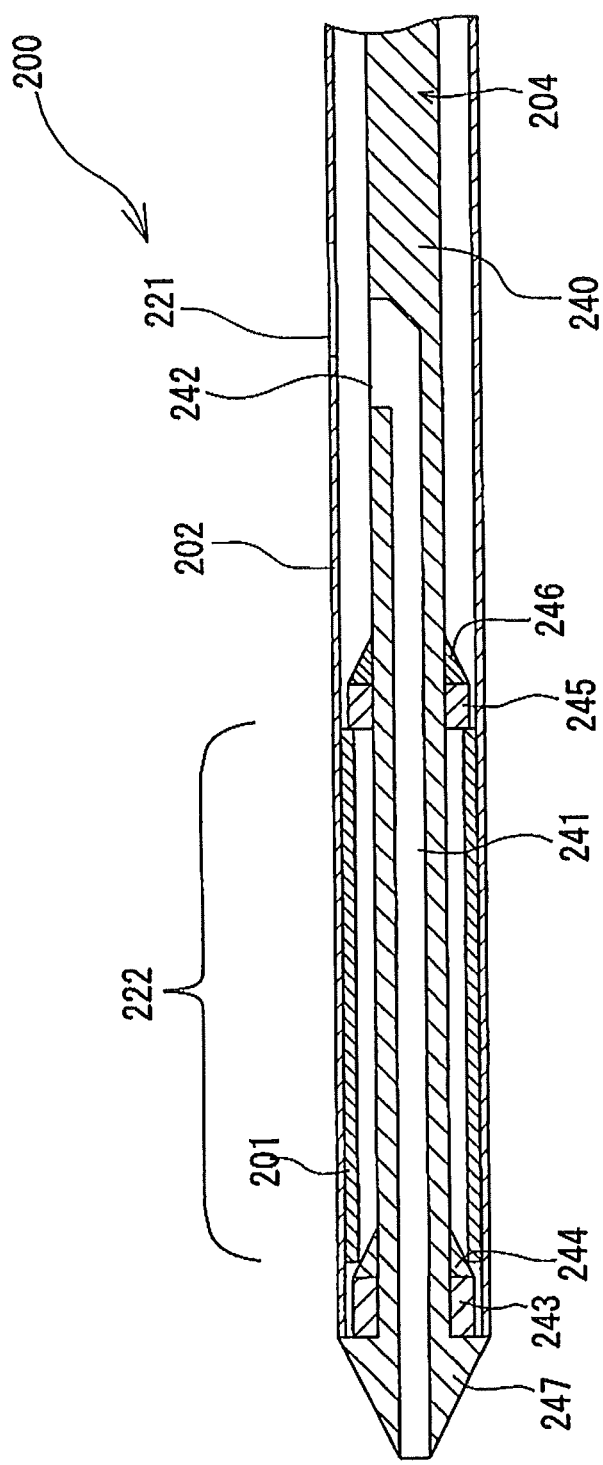
FIG. 14 is an enlarged longitudinal cross-sectional view of a distal portion of the stent delivery system shown in FIG. 13.

FIGS. 13 and 14 illustrate one form of a stent delivery system 200 that includes a sheath 202, a stent 201 contained in a distal portion of the sheath 202, and an inner tube 204 slidably inserted in the sheath 202 and which is for discharging the stent 201 through the distal end of the sheath 202.

As the stent 201, there is used the above-mentioned self-expandable stent which is formed to be cylindrical in shape, is compressed toward its center axis at the time of insertion into a living body, and is capable of automatically expanding outward when placed (put indwelling) in the living body, to be restored into its pre-compression shape. The particular form of the stent is preferably the form of the above-described stent 1 shown in FIGS. 1-8. In the stent 1 in this embodiment, the one end portions 34, 44 of the struts constitute the distal end of the stent so that the one end portions 34, 44 of the struts are at the distal end of the stent. The other end portions 33, 43 of the struts provided with the respective engaging hole or through opening 8 constitute the proximal end of the stent so that the other end portions 34, 44 of the struts are at the proximal end of the stent.

As shown in FIG. 13, the stent delivery system 200 in this example has the sheath 202, the self-expandable stent 201, and the inner tube 204. As shown in FIGS. 13 and 14, the sheath 202 is a tubular body, which open at its front end (tip) and its rear end. The tip opening functions as a discharge port for the stent 201 when the stent 201 is placed (put indwelling) in a stenosis in a body lumen. Discharging the stent via the tip opening releases the stent 201 from a stress load (compression load), allowing the stent to expand and to be restored to its pre-compression shape. The distal portion of the sheath 202 constitutes a stent containing part 222 in which is positioned or contained the stent 201n. In addition, the sheath 202 has a side hole 221 provided on the proximal side (proximally) relative to the containing part 222. The side hole 221 is for leading out a guide wire to the exterior.

The outside diameter of the sheath 202 is preferably about 0.5 to 4.0 mm, particularly 0.8 to 3.0 mm. The inside diameter of the sheath 202 is preferably about 0.5 to 2.5 mm. The length of the sheath 202 is preferably 300 to 2500 mm, particularly 300 to 2000 mm.

In addition, as shown in FIG. 13, a sheath hub 206 is fixed to a proximal portion of the sheath 202. The sheath hub 206 has a sheath hub body, and a valve body which is contained in the sheath hub body and holds the inner tube 204 in a slidable and liquid-tight manner. The sheath hub 206 has a side port 261 branched toward an obliquely rear side from the vicinity of the center of the sheath hub body. In addition, the sheath hub 206 preferably has an inner tube locking mechanism for restricting the movement of the inner tube 204.

As shown in FIGS. 13 and 14, the inner tube 204 includes a shaft-like inner tube body section 240, a distal portion 247 provided at the distal end of the inner tube body section 240 and protruding distally beyond the distal end of the sheath 202, and an inner tube hub 207 fixed to a proximal portion of the inner tube body section 240.

The distal portion 247 protrudes from the distal end of the sheath 202, and is preferably formed in a tapered shape which is gradually reduced in diameter toward the distal end, as shown in FIG. 14. With the distal portion 247 formed in such a shape, insertion into a stenosis is facilitated. In addition, the inner tube 204 preferably has a stopper which is provided on the distal side relative to the stent 201 and which prevents the sheath from moving in the distal direction. The proximal end of the distal portion 247 of the inner tube 204 can abut on the distal end of the sheath 202, and functions as the above-mentioned stopper.

As shown in FIG. 14, the inner tube 204 has two axially spaced apart projections 243, 245 for holding the self-expandable stent 201. The projections 243, 245 are preferably annular projections. Specifically, the stent-holding projection 243 is provided on the proximal side of the distal portion 247 of the inner tube 204. The stent-discharging projection 245 is provided at a position spaced by a predetermined distance to the proximal side from the stent-holding projection 243. The stent 201 is disposed between these two projections 243, 245. The outside diameter of each of the projections 243, 245 is so sized that the projections 243, 245 can abut on the stent 201 in the compressed state as described in more detail below. This helps ensure that the stent 201 is restrained by the projection 243 from moving toward the distal side and is restrained by the projection 245 from moving toward the proximal side. Further, when the sheath 202 is moved toward the proximal side, the stent 201 is held in situ by the projection 245, so that the stent 201 is exposed from the sheath 202 and discharged. Furthermore, as shown in FIG. 14, the proximal side of the stent-discharging projection 245 is preferably provided with a tapered portion 246 which is gradually reduced in diameter toward the proximal side. Similarly, the proximal side of the stent-holding projection 243 is preferably provided with a tapered portion 244 which is gradually reduced in diameter toward the proximal side as shown in FIG. 14. This configuration helps ensure that, when the inner tube 204 is re-contained into the sheath 202 after protruding the inner tube 204 from the distal end of the sheath 202 so as to discharge the stent 201 from the sheath, the projection is prevented from being caught by the distal end of the sheath. In addition, the projections 243, 245 may be formed as separate members by a radiopaque material. The position of the stent can thus be accurately grasped under radioscopy, whereby the procedure is facilitated.

As shown in FIG. 14, the inner tube 204 has a lumen 241 which extends from the distal end of the inner tube to at least the proximal side relative to the stent containing part 222 of the sheath 202, and an inner tube side hole 242 which communicates with the lumen 241 on the proximal side relative to the stent containing part. In the stent delivery system 200 in this example, the lumen 241 is terminated at a part where the side hole 242 is formed. The lumen 241 is for permitting a process in which one end of a guide wire is inserted into the inner tube 204 via the distal end of the stent delivery system 200, is passed partly through the inside of the inner tube, and is led out to the exterior via a side surface of the inner tube. The inner tube side hole 242 is located slightly on the distal side along the stent delivery system 200, relative to the sheath side hole 221. The center of the inner tube side hole 242 is preferably located at a position deviated by 0.5 to 10 mm to the distal side from the center of the sheath side hole 221.

The stent delivery system is not limited to the above-mentioned type, and the above-mentioned lumen 241 may extend to the proximal end of the inner tube. In this case, the sheath side hole 221 is unnecessary.

The inner tube 204 penetrates the sheath 202 to protrude from the rear end opening of the sheath 202. As shown in FIG. 13, the inner tube hub 207 is firmly attached to a proximal portion of the inner tube 204.

Figure 15:
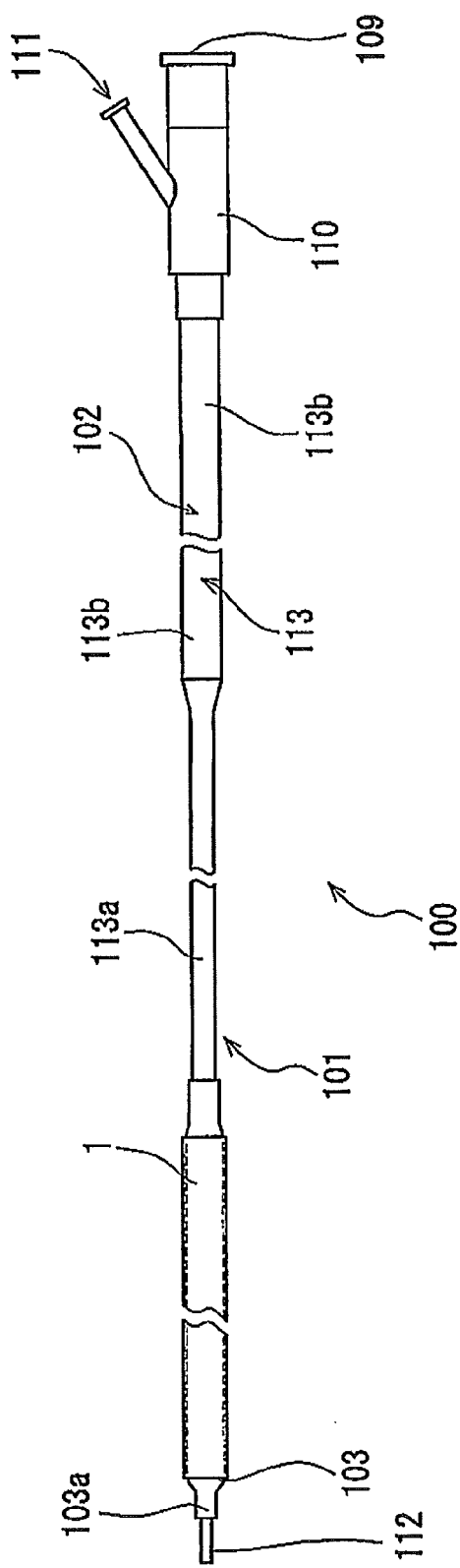
FIG. 15 is a front view of a stent delivery system according to another example disclosed here.
Figure 16:
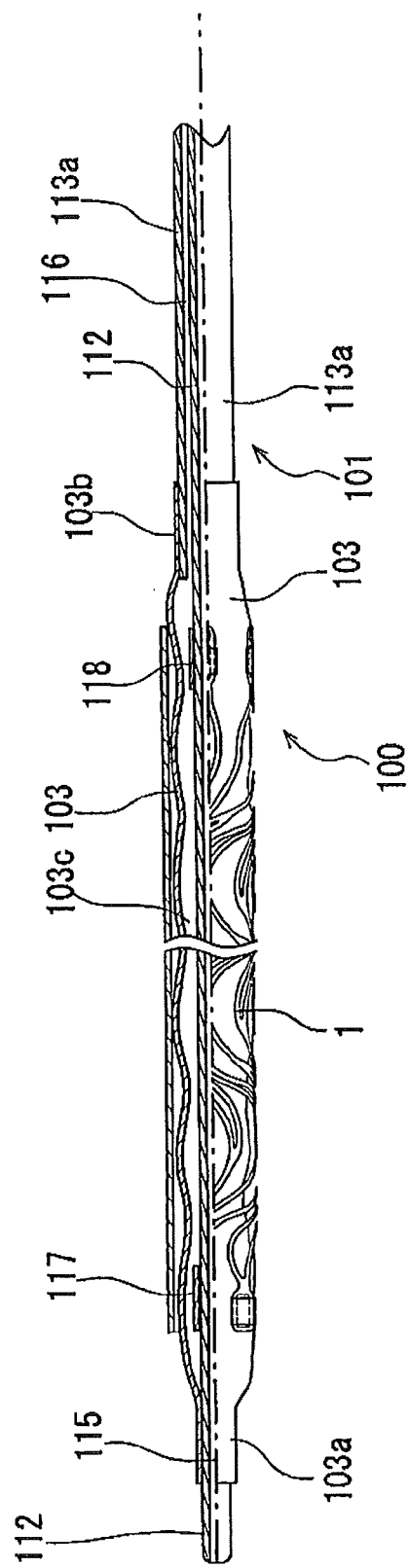
FIG. 16 is an enlarged partial cross-sectional view of a distal portion of the stent delivery system shown in FIG. 15.
Figure 17:
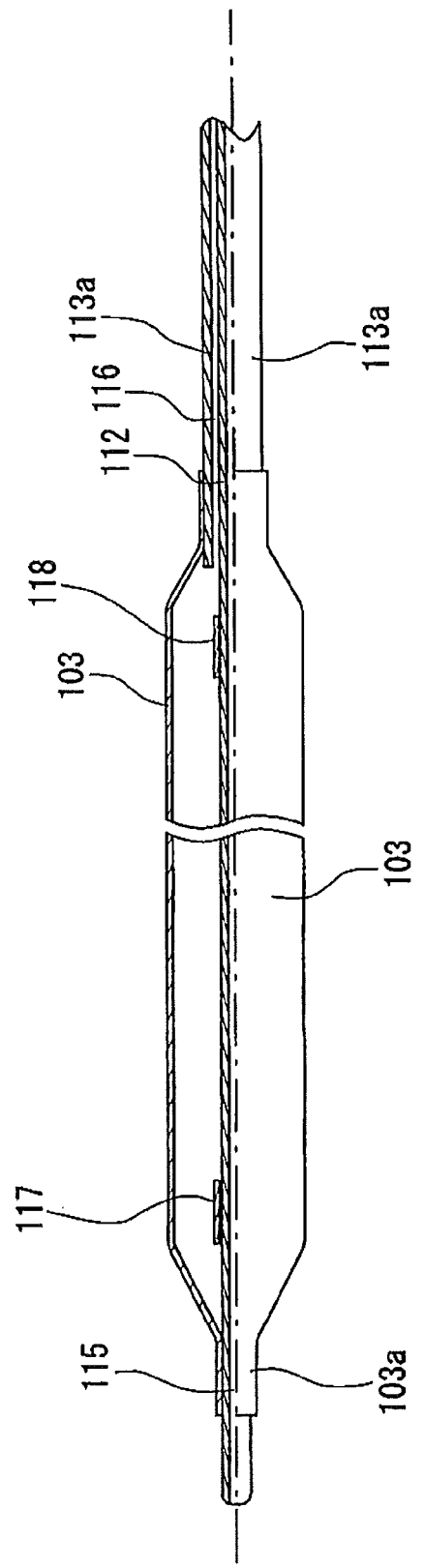
FIG. 17 is an illustration for describing the operation of the stent delivery system.

An example of another stent delivery system disclosed here is shown in FIGS. 15-17. This stent delivery system 100 includes a tubular shaft body section 102, a foldable and dilatable balloon 103 provided at a distal portion of the shaft body section 102, and a stent 1 mounted to envelope the balloon 103 in the folded state and which is expanded by dilation of the balloon 103.

The stent 1 used in this stent delivery system can be the above-described stent 1 or any of the other embodiments or examples of stents described above. The stent delivery system 100 in this example is composed of the above-described stent 1, and a tubular stent delivery system body 101 on which the stent 1 is mounted.

The stent delivery system body 101 has the tubular shaft body section 102, and the foldable and dilatable balloon 103 provided at a distal portion of the shaft body section, and the stent 1 is so mounted as to envelope the balloon 103 in the folded state and is expanded by dilation of the balloon 103. The stent to be used here is a so-called balloon-expandable stent which has a diameter permitting insertion of the stent into a lumen in a living body and which can be expanded when a radially outwardly directed spreading force is exerted on the stent from the inside of the tubular body.

In the stent delivery system 100 in this example, as shown in FIGS. 15 and 16, the shaft body section 102 has a guide wire lumen 115 which has one end opening at the front end (tip) of the shaft body section 102 and which has the other end opening at the rear end of the shaft body section 102.

The stent delivery system body 101 has the shaft body section 102, and the stent-expanding balloon 103 fixed to a distal portion of the shaft body section 102, with the stent 1 being mounted on the balloon 103. The shaft body section 102 has an inner tube 112 and an outer tube 113 and a branch hub 110.

As shown in FIGS. 15 and 16, the inner tube 112 is a tubular body in which is provided the guide wire lumen 115 through which is inserted and passed a guide wire. The inner tube 112 has a length of 100 to 2500 mm, preferably 250 to 2000 mm, an outside diameter of 0.1 to 1.0 mm, preferably 0.3 to 0.7 mm, and a material thickness of 10 to 250 μm, preferably 20 to 100 μm. The inner tube 112 is inserted in the outer tube 113, and its distal portion protrudes from the outer tube 113, distally beyond the distal end of the outer tube 113. The outer surface of the inner tube 112 and the inner surface of the outer tube 113 define a balloon-dilating lumen 116, which has a sufficient internal volume. The outer tube 113 is a tubular body in which the inner tube 112 is inserted and which has a distal end located at a position slightly retracted from the distal end of the inner tube 112.

The outer tube 113 has a length of 100 to 2500 mm, preferably 250 to 2000 mm, an outside diameter of 0.5 to 1.5 mm, preferably 0.7 to 1.1 mm, and a material thickness of 25 to 200 preferably 50 to 100 μm.

In the stent delivery system 100 in this example, the outer tube 113 is composed of a distal-side outer tube 113a and a body-side outer tube 113b which are joined to each other. The distal-side outer tube 113a is reduced in diameter in a tapered form at its portion on the distal side relative to a joint part at which the distal-side outer tube 113a is joined to the body-side outer tube 113b, and is relatively small in diameter on the distal side relative to the tapered portion.

The outside diameter at the small-diameter portion of the distal-side outer tube 113a is 0.50 to 1.5 mm, preferably 0.60 to 1.1 mm. The outside diameter of a proximal portion of the distal-side outer tube 113a and the body-side outer tube 113b is 0.75 to 1.5 mm, preferably 0.9 to 1.1 mm.

The balloon 103 has a tip-side joint part 103a and a rear-end-side joint part 103b. The tip-side joint part 103a is fixed to a position slightly on the rear end side relative to the distal end of the inner tube 112, and the rear-end-side joint part 103b is fixed to the distal end of the outer tube 113. In addition, the balloon 103 communicates with the balloon-dilating lumen 116 in the vicinity of its proximal portion.

The material for forming the inner tube 112 and the outer tube 113 is preferably a material which has a certain degree of flexibility. Examples of the material which can be used here include thermoplastic resins such as polyolefins (e.g., polyethylene, polypropylene, ethylene-propylene copolymer, ethylene-vinyl acetate copolymer or the like), polyvinyl chloride, polyamide elastomers, polyurethane, etc., silicone rubber, latex rubber, etc., among which preferred are the thermoplastic resins, and more preferred are the polyolefins.

The balloon 103 is foldable, as shown in FIG. 16. In a non-dilated state, the balloon 103 is foldable onto the outer periphery of the inner tube 112. As shown in FIG. 16, the balloon 103 has a dilatable section which is a tubular section (preferably, a cylindrical section) having a constant diameter (inclusive of substantially constant diameter) so that the dilatable section is able to expand the stent 1 mounted thereon. The substantially cylindrical section may not necessarily be a perfect cylinder, and may be prismatic in shape. As above-mentioned, the tip-side joint part 103a of the balloon 103 is firmly attached to the inner tube 112, and the rear-end-side joint part 103b of the balloon 103 is firmly attached to the distal end of the outer tube 113, in a liquid-tight manner, by an adhesive or by heat fusing or the like. The balloon 103 is formed in a tapered shape between the dilatable section and each of the joint parts.

The balloon 103 forms a dilation space 103c between the inner surface of the balloon 103 and the outer surface of the inner tube 112. The dilation space 103c, at its rear end portion, communicates with the dilating lumen 116 along the whole circumference thereof. Thus, the rear end of the balloon 103 communicates with the dilating lumen having a comparatively large internal volume, so that injection of a dilating fluid into the balloon from the dilating lumen 116 is carried out quite assuredly.

The material forming the balloon 103 is preferably a material which has a certain degree of flexibility. Examples of the material which can be used here include thermoplastic resins such as polyolefins (e.g., polyethylene, polypropylene, ethylene-propylene copolymer, ethylene-vinyl acetate copolymer, crosslinked ethylene-vinyl acetate copolymer or the like), polyvinyl chloride, polyamide elastomers, polyurethane, polyesters (e.g., polyethylene terephthalate), polyarylene sulfides (e.g., polyphenylene sulfide), etc., silicone rubber, latex rubber, etc. Particularly, orientable materials are preferable, and the balloon 103 is preferably a biaxially oriented one that has high strength and dilation force.

As for the size of the balloon 103, the cylindrical section (dilatable section) in the dilated state has an outside diameter of 2 to 4 mm, preferably 2.5 to 3.5 mm, and a length of 10 to 50 mm, preferably 20 to 40 mm. In addition, the tip-side joint part 103a has an outside diameter of 0.9 to 1.5 mm, preferably 1 to 1.3 mm, and a length of 1 to 5 mm, preferably 1 to 3 mm. Besides, the rear-end-side joint part 103b has an outside diameter of 1 to 1.6 mm, preferably 1.1 to 1.5 mm, and a length of 1 to 5 mm, preferably 2 to 4 mm.

As shown in FIGS. 16 and 17, the stent delivery system 100 has two radiopaque members 117, 118 fixed to the outer surface of the shaft body section at positions corresponding to both ends of the cylindrical section (dilatable section) in the dilated state. The stent delivery system 100 may have two radiopaque members fixed to the outer surface of the shaft body section 102 (in this example, the inner tube 112) at positions corresponding to both ends of a predetermined length of central portion of the stent 1. Furthermore, the stent delivery system 100 may have a single radiopaque member fixed to the outer surface of the shaft body section at a position corresponding to a central portion of the stent.

The radiopaque members 117, 118 are each preferably a ring-shaped or annular member having a predetermined length or a member obtained by winding a linear body into a coil shape. The material forming the radiopaque members 117, 118 is preferably, for example, gold, platinum, tungsten or their alloys, or a silver-palladium alloy or the like.

The stent 1 is so mounted as to envelope the balloon 103. The stent is produced by processing a metallic pipe having an inside diameter which is smaller than the diameter of the stent in the expanded state and which is greater than the outside diameter of the balloon in the folded state. The balloon is inserted into the stent thus produced, and a uniform force is exerted on the outer surface of the stent in inward directions so as to reduce the diameter of the stent, thereby forming a stent in a product state. In other words, the stent 1 is completed by compressingly mounting it onto the balloon.

A linear rigidity-imparting body (not shown) may be inserted between the inner tube 112 and the outer tube 113 (in the balloon-dilating lumen 116). The rigidity-imparting body prevents the body section 102 of the stent delivery system 100 from extremely bending at a bending part and facilitates pushing-in of the distal portion of the stent delivery system 100, without considerably lowering the flexibility of the stent delivery system 100. A distal portion of the rigidity-imparting body is preferably made smaller in diameter than the other portion by such a method as polishing. In addition, the distal end of the small diameter portion of the rigidity-imparting body is preferably extending to the vicinity of a distal portion of the outer tube 113. The rigidity-imparting body is preferably a metal wire. The metal wire is a wire of an elastic metal such as stainless steel, etc., a superelastic alloy or the like, with a diameter of 0.05 to 1.50 mm, preferably 0.10 to 1.00 mm. Particularly preferred are wires of high-tensile stainless steel for spring use and of superelastic alloys.

In the stent delivery system 100 in this example, the branch hub 110 is fixed to the proximal end, as shown in FIG. 15. The branch hub 110 is composed of: an inner tube hub which has a guide wire inlet 109 communicating with the guide wire lumen 115 and forming a guide wire port and is firmly attached to the inner tube 112; and an outer tube hub which communicates with the balloon-dilating lumen 116, has an injection port 111 and is firmly attached to the outer tube 113. In addition, the outer tube hub and the inner tube hub are firmly attached to each other. As the material for forming the branch hub 110, there can be preferably used thermoplastic resins such as polycarbonates, polyamides, polysulfones, polyarylates, methacrylate-butylene-styrene copolymer, etc.

The structure of the stent delivery system is not limited to the above-described. For example, the stent delivery system may be provided in its intermediate portion with a guide wire insertion port which communicates with the guide wire lumen.

The detailed description above describes features and aspects of embodiments of a stent and stent delivery system. The invention is not limited, however, to the precise embodiments and variations described. Various changes, modifications and equivalents could be effected by one skilled in the art without departing from the spirit and scope of the invention as defined in the appended claims. It is expressly intended that all such changes, modifications and equivalents which fall within the scope of the claims are embraced by the claims.

What is claimed is:

1. A stent for placement in living body comprising:
a plurality of sinusoidal first wave-shaped struts which are all commonly configured and a plurality of sinusoidal second wave-shaped struts which are all commonly configured, the first wave-shaped struts and the second wave-shaped struts together forming a tubular member, the first wave-shaped struts circumferentially alternating with the second wave-shaped struts so that one of the second wave-shaped struts is positioned between each circumferentially adjacent pair of first wave-shaped struts and so that one of the first wave-shaped struts is positioned between each circumferentially adjacent pair of second wave-shaped struts;
each of the first wave-shaped struts extending in an axial direction of the tubular member from one end of the tubular member to an opposite end of the tubular member, each of the first wave-shaped struts having a first end positioned at the one end of the tubular member and a second end positioned at the opposite end of the tubular member, each of the first wave-shaped struts comprising a plurality of axially spaced apart first curved portions which are convexly curved towards one circumferential side of the first wave-shaped strut and a plurality of axially spaced apart second curved portions which are convexly curved towards an opposite circumferential side of the first wave-shaped struts;
each of the second wave-shaped struts extending in the axial direction of the tubular member from the one end of the tubular member to the opposite end of the tubular member, each of the second wave-shaped struts having a first end positioned at the one end of the tubular member and a second end positioned at the opposite end of the tubular member, each of the second wave-shaped struts comprising a plurality of axially spaced apart first curved portions which are convexly curved towards one circumferential side of the second wave-shaped strut and a plurality of axially spaced apart second curved portions which are convexly curved towards an opposite circumferential side of the second wave-shaped strut;
the first and second curved portions of the first wave-shaped strut each possessing an apex, and the first and second curved portions of the second wave-shaped strut each possessing an apex;
each of the first wave-shaped struts being connected to each of the circumferentially adjacent second wave-shaped struts by at least one connecting strut;
the first end of each respective first wave-shaped strut being connected to the first end of the second wave-shaped strut which is on the one circumferential side of the respective first wave-shaped strut, and the second end of each respective first wave-shaped strut being connected to the second end of the second wave-shaped strut which is on the opposite circumferential side of the respective first wave-shaped strut; and
the apex of each first curved portion of the first wave-shaped struts being axially offset relative to an axially closest apex of the first curved portion of the circumferentially adjacent second wave-shaped strut.

2. The stent according to claim 1, wherein each of the first wave-shaped struts is connected to each of the circumferentially adjacent second wave-shaped struts by a plurality of connecting struts.

3. A stent for placement in living body comprising: a plurality of first wave-shaped struts and a plurality of second wave-shaped struts which together form a tubular member; the first wave-shaped struts extending in an axial direction of the tubular member from one end of the tubular member to an opposite end of the tubular member; the plurality of first wave-shaped struts being arranged and spaced apart from each other in a circumferential direction of the tubular member; each of the second wave-shaped struts being located between the first wave-shaped struts, extending in the axial direction of the tubular member from the one end of the tubular member to the opposite end of the tubular member, and being arranged and spaced apart in the circumferential direction of the tubular member; each of the second wave-shaped struts being positioned between two circumferentially adjacent ones of the first wave-shaped struts; a plurality of connecting struts each interconnecting one of the first wave-shaped struts and one of the second wave-shaped struts which are circumferentially adjacent to each other; the connecting struts extending in the axial direction over a predetermined length; the first and second wave-shaped struts each comprising a plurality of apexes; the apexes of the second wave-shaped struts being shifted a predetermined distance in the axial direction of the tubular member relative to apexes of the first wave-shaped struts which are axially closest and curved in a common direction; and the first wave-shaped struts each having an end portion at one end that is joined to an end portion at one end of the second wave-shaped struts.

4. The stent according to claim 3, wherein each connecting strut: has one end connected in the vicinity of an inflection point of one of the first wave-shaped struts and an opposite end connected to one of the second wave-shaped struts in a region ranging from a position near one apex of the second wave-shaped strut and to a position slightly beyond the one apex of the second wave-shaped strut; extends in the axial direction; and is curved in the same direction as the one apex of the second wave-shaped strut.

5. The stent according to claim 3, wherein each connecting strut: has one end connected to one of the first wave-shaped struts at a point spaced from all of the apexes of the first wave-shaped strut and an opposite end connected to one of the second wave-shaped struts in a region ranging from a position near one apex of the second wave-shaped strut and to a position slightly beyond the one apex of the second wave-shaped strut; extends in the axial direction; and is curved in the same direction as the one apex of the second wave-shaped strut.

6. The stent according to claim 3, wherein each connecting strut is curved in a different curving direction relative to the connecting strut that is circumferentially closest and is curved in a common curving direction relative to the connecting strut that is axially closest.

7. The stent according to claim 3, wherein each first wave-shaped strut includes end portions, the first wave-shaped struts possessing a wavelength and amplitude that are the same along the entire first wave-shaped strut except for the end portions.

8. The stent according to claim 7, wherein each second wave-shaped strut includes end portions, the second wave-shaped struts possessing a wavelength and amplitude that are the same along the entire second wave-shaped strut except for the end portions.

9. The stent according to claim 3, wherein the first wave-shaped struts and the second wave-shaped struts possess a common wavelength.

10. The stent according to claim 3, wherein the first and second wave-shaped struts each possess a phase, the phase of the second wave-shaped struts being shifted in the axial direction of the stent relative to the phase of the first wave-shaped struts.

11. The stent according to claim 3, wherein the first wave-shaped struts each possess a waveform comprised of an amplitude and a wavelength, at least a part of each first wave-shaped strut being different in waveform from a remainder of the first wave-shaped strut.

12. The stent according to claim 11, wherein the second wave-shaped struts each possess a waveform comprised of an amplitude and a wavelength, at least a part of each second wave-shaped strut being different in waveform from a remainder of the second wave-shaped strut.

13. The stent according to claim 3, wherein the first wave-shaped struts and the second wave-shaped struts possess a common wavelength and a common amplitude, the second wave-shaped struts being shifted in phase in the axial direction of the stent relative to the first wave-shaped struts.

14. The stent according to claim 3, wherein the first wave-shaped struts and the second wave-shaped struts extend parallel to a center axis of the stent.

15. The stent according to claim 3, wherein a plurality of the connecting struts connect each of the first wave-shaped struts to each of the circumferentially adjacent second wave-shaped struts, the plurality of connecting struts connecting each first wave-shaped strut to each circumferentially adjacent second wave-shaped strut being arranged in spaced apart series in the axial direction of the stent.

16. The stent according to claim 3, wherein a plurality of the connecting struts connect each of the first wave-shaped struts to each of the circumferentially adjacent second wave-shaped strut, the plurality of connecting struts connecting each first wave-shaped strut to each circumferentially adjacent second wave-shaped strut being arranged in the circumferential direction of the tubular member.

17. The stent according to claim 3, wherein the apexes of each first wave-shaped strut are positioned in troughs of the circumferentially adjacent second wave-shaped strut, and the apexes of the second wave-shaped strut are positioned in troughs of the circumferentially adjacent first wave-shaped struts.

18. The stent according to claim 3, wherein each of a plurality of the connecting struts are curved in a circular arc shape possessing a radius of curvature equal to a radius of curvature of a curved part of the first wave-shaped strut or the second wave-shaped strut to which the connecting strut is connected.

19. The stent according to claim 3, wherein the first wave-shaped struts include a first wave-shaped strut on one circumferential side of one of the second wave-shaped struts and a first wave-shaped strut on an opposite circumferential side of the one second wave-shaped strut, the one end portion of the one second wave-shaped strut being connected by a first joint section to the one end portion of the first wave-shaped strut on the one circumferential side of the one second wave-shaped strut, and an opposite end portion of the one second wave-shaped strut being connected by a second joint section to an opposite end portion of the first wave-shaped strut on the opposite circumferential side of the one second wave-shaped strut, the first and second joint sections each including a radiopaque marker.

20. The stent according to claim 3, wherein each of the first wave-shaped struts includes opposite end portions each connected to a different one of the second wave-shaped struts.

21. The stent according to claim 3, wherein the stent has a surface configuration which accelerates endothelial growth.

22. The stent according to claim 3, wherein the stent is a self-expandable stent possessing a cylindrical shape.

23. The stent according to claim 3, wherein the stent is a balloon-expandable stent comprising a tubular body possessing a diameter sized for insertion into a lumen in a living body, and is outwardly expandable when a radially outwardly spreading force is exerted on the stent from inside the stent.

24. A stent delivery system comprising:
an inner tube;
a sheath possessing a distal portion surrounding the inner tube so that the inner tube is positioned inside and covered by the distal portion of the sheath; and
the stent according to claim 22 mounted on the inner tube and positioned inside the distal portion of the sheath, the sheath being movable in a proximal direction relative to the inner tube to discharge the stent.

25. A stent delivery system comprising:
a tubular shaft body section possessing a distal portion;
a foldable and dilatable balloon at a distal portion of the shaft body section; and
the stent according to claim 23 mounted in surrounding relation to the balloon, the stent being in a folded state and being outwardly expandable by dilation of the balloon.

* * * * *